(12) United States Patent
Yuan et al.

(10) Patent No.: US 12,217,591 B2
(45) Date of Patent: Feb. 4, 2025

(54) SYSTEMS AND METHODS FOR TERMINAL CONTROL

(71) Applicant: SHENZHEN SHOKZ CO., LTD., Guangdong (CN)

(72) Inventors: Yongshuai Yuan, Shenzhen (CN); Wenjun Deng, Shenzhen (CN); Wenbing Zhou, Shenzhen (CN); Yujia Huang, Shenzhen (CN); Fengyun Liao, Shenzhen (CN); Xin Qi, Shenzhen (CN)

(73) Assignee: SHENZHEN SHOKZ CO., LTD., Shenzhen (CN)

( * ) Notice: Subject to any disclaimer, the term of this patent is extended or adjusted under 35 U.S.C. 154(b) by 196 days.

(21) Appl. No.: 17/814,222

(22) Filed: Jul. 21, 2022

(65) Prior Publication Data

US 2023/0049441 A1 Feb. 16, 2023

Related U.S. Application Data

(63) Continuation of application No. PCT/CN2021/112094, filed on Aug. 11, 2021.

(51) Int. Cl.
*G08B 21/04* (2006.01)
*A61B 5/00* (2006.01)
(Continued)

(52) U.S. Cl.
CPC ........ *G08B 21/0453* (2013.01); *A61B 5/7282* (2013.01); *G01H 1/12* (2013.01); *G06F 3/011* (2013.01)

(58) Field of Classification Search
CPC .... G08B 21/0453; A61B 5/7282; G01H 1/12; G06F 3/011
(Continued)

(56) References Cited

U.S. PATENT DOCUMENTS 6,704,671 B1 * 3/2004 Umminger, III ..... G11B 27/036
367/901
7,346,176 B1 * 3/2008 Bernardi .............. H04R 29/006
381/313
(Continued)

FOREIGN PATENT DOCUMENTS

CN 203561744 U 4/2014
CN 104814741 A 8/2015
(Continued)

OTHER PUBLICATIONS

International Search Report in PCT/CN2021/112094 mailed on Apr. 25, 2022, 8 pages.
(Continued)

*Primary Examiner* — Kerri L McNally
*Assistant Examiner* — Thang D Tran
(74) *Attorney, Agent, or Firm* — METIS IP LLC

(57) ABSTRACT

The embodiments of the present disclosure disclose a system and method. The system may include at least one storage device configured to storage computer instruction; and at least one processor, in communication with the storage device. When executing the computer instructions, the at least one processor is configured to direct the system to perform operations including: obtaining a sensing signal of at least one sensing device; identifying a signal feature of the sensing signal; and determining, based on the signal feature, an operation of a target object associated with the at least one sensing device.

17 Claims, 19 Drawing Sheets

(51) Int. Cl.
*G01H 1/12* (2006.01)
*G06F 3/01* (2006.01)

(58) Field of Classification Search
USPC .................................................. 340/539.12
See application file for complete search history.

(56) References Cited

U.S. PATENT DOCUMENTS

| | | | | |
|---|---|---|---|---|
| 9,998,577 | B1* | 6/2018 | Harmke | H04W 4/10 |
| 2001/0026264 | A1* | 10/2001 | Rosenberg | G06F 3/0354 |
| | | | | 345/156 |
| 2001/0045935 | A1* | 11/2001 | Chang | G06F 3/016 |
| | | | | 345/156 |
| 2002/0189551 | A1* | 12/2002 | Patterson | A01K 15/023 |
| | | | | 119/719 |
| 2004/0130455 | A1 | 7/2004 | Prochazka | |
| 2006/0259205 | A1* | 11/2006 | Krum | G06F 3/011 |
| | | | | 701/1 |
| 2008/0309761 | A1* | 12/2008 | Kienzle | G08B 13/194 |
| | | | | 348/143 |
| 2009/0027233 | A1* | 1/2009 | Li | G09B 21/003 |
| | | | | 341/20 |
| 2009/0296951 | A1* | 12/2009 | De Haan | G06F 3/017 |
| | | | | 381/74 |
| 2010/0298683 | A1* | 11/2010 | Cabrera | A61B 5/02055 |
| | | | | 600/364 |
| 2011/0211282 | A1* | 9/2011 | Nanov | H02M 1/32 |
| | | | | 361/18 |
| 2013/0009861 | A1 | 1/2013 | Valik et al. | |
| 2014/0139454 | A1 | 5/2014 | Mistry et al. | |
| 2015/0180932 | A1* | 6/2015 | Yost | H04L 65/80 |
| | | | | 370/352 |
| 2015/0366518 | A1* | 12/2015 | Sampson | A61B 5/7264 |
| | | | | 600/509 |
| 2016/0124707 | A1 | 5/2016 | Ermilov et al. | |
| 2016/0334901 | A1* | 11/2016 | Rihn | G06F 3/011 |
| 2017/0048608 | A1* | 2/2017 | Yang | H04R 1/1016 |
| 2017/0094393 | A1 | 3/2017 | Panecki et al. | |
| 2017/0115743 | A1* | 4/2017 | Kasar | G06F 1/1632 |
| 2017/0161017 | A1* | 6/2017 | Chereau | G06F 3/167 |
| 2017/0242486 | A1* | 8/2017 | Grant | G06F 3/0338 |
| 2017/0261473 | A1 | 9/2017 | Sung et al. | |
| 2017/0280222 | A1* | 9/2017 | Boesen | G06F 3/011 |
| 2018/0014113 | A1* | 1/2018 | Boesen | A61B 5/4866 |
| 2018/0054513 | A1* | 2/2018 | Ma | H04W 12/33 |
| 2018/0091381 | A1 | 3/2018 | McLaughlin et al. | |
| 2018/0350203 | A1* | 12/2018 | Cruz-Hernandez | A63F 13/28 |
| 2019/0057700 | A1* | 2/2019 | Kent | G06F 3/167 |
| 2019/0325716 | A1* | 10/2019 | Khoshkava | G08B 6/00 |
| 2019/0385376 | A1 | 12/2019 | Kim et al. | |
| 2020/0090484 | A1* | 3/2020 | Chen | G06T 7/50 |
| 2020/0174551 | A1* | 6/2020 | Kozloski | G06T 19/20 |
| 2020/0372250 | A1 | 11/2020 | Jiang et al. | |
| 2021/0052221 | A1* | 2/2021 | Panneer Selvam | A61B 5/1117 |
| 2021/0081747 | A1* | 3/2021 | Karani | G06F 16/9554 |
| 2021/0096811 | A1* | 4/2021 | Giles | G06F 3/167 |
| 2021/0219923 | A1* | 7/2021 | Eun Young Yang | A61B 5/0006 |
| 2021/0221228 | A1* | 7/2021 | Barry | G06F 3/016 |
| 2021/0279554 | A1* | 9/2021 | Ibtehaz | A61B 5/7278 |
| 2022/0167084 | A1* | 5/2022 | Yang | H04R 1/1016 |
| 2022/0274522 | A1* | 9/2022 | Paul | B60Q 1/0082 |
| 2022/0301574 | A1* | 9/2022 | Zheng | G10L 21/0216 |
| 2023/0026400 | A1* | 1/2023 | Kuehner | B62D 6/008 |
| 2023/0033782 | A1* | 2/2023 | Wang | G06F 3/03 |
| 2023/0045099 | A1* | 2/2023 | Ankem | G06N 3/045 |

FOREIGN PATENT DOCUMENTS

| | | |
|---|---|---|
| CN | 106955108 A | 7/2017 |
| CN | 107049280 A | 8/2017 |
| CN | 109480403 A | 3/2019 |
| CN | 109996382 A | 7/2019 |
| CN | 111768757 A | 10/2020 |
| TW | 200839663 A | 10/2008 |
| WO | 2021147636 A1 | 7/2021 |

OTHER PUBLICATIONS

Written Opinion in PCT/CN2021/112094 mailed on Apr. 25, 2022, 10 pages.
The Partial Supplementary European Search Report in European Application No. 21920146.4 mailed on Mar. 21, 2023, 12 pages.
Decision of Grant in Russian Application No. 2022121093 mailed on Sep. 22, 2023, 22 pages.
The Office Action in Russian Application No. 2022121093 mailed on Mar. 22, 2023, 14 pages.
Notice of Reasons for Rejection in Japanese Application No. 2022562834 mailed on Jun. 3, 2024, 8 pages.
Notice of Preliminary Rejection in Korean Application No. 10-2022-7032021 mailed on Nov. 4, 2024, 12 pages.

* cited by examiner

SYSTEMS AND METHODS FOR TERMINAL CONTROL

CROSS-REFERENCE TO RELATED APPLICATIONS

This application is a continuation of International Application No. PCT/CN2021/112094, filed on Aug. 11, 2021, the contents of which are hereby incorporated by reference.

TECHNICAL FIELD

The present disclosure generally relates to the field of sensing devices, and in particular, relates to systems and methods for controlling a terminal device based on a sensing signal collected by a sensing device.

BACKGROUND

More and more smart terminal devices appear in daily life, and it is beneficial to efficiently and conveniently control smart terminal devices to improve user experiences. A commonly used human-computer interaction is implemented by means of voice dialogues or manual operations of entity structures set on the terminal device. However, in some cases, such as high noise, low environment brightness, or inconvenience for user operations, etc., it may be difficult and problematic to use voice dialogues or manual operations on a panel to control the terminal device.

The present disclosure provides a method for determining an operation of a target subject, which may improve the accuracy of the determined operation of the target subject, so that the operation of the target object satisfy user's expectations.

SUMMARY

Some of the embodiments of the present disclosure provide a system. The system may include: at least one storage device configured to storage computer instructions; and at least one processor in communication with the storage device, wherein when executing the computer instructions, the at least one processor is configured to direct the system to perform operations including: obtaining a sensing signal of at least one sensing device; identifying s signal feature of s sensing signal; and determining, based on the signal feature, an operation of a target object associated with the at least one sensing device.

In some embodiments, the at least one sensing device may include a vibration sensing device.

In some embodiments, the signal feature may include at least one of a count of vibration peaks, a signal strength, a time interval between two adjacent vibration peaks, frequency components, or a signal duration.

In some embodiments, the vibration sensing device may be connected to a vibration receiving area through a solid medium, and receive a vibration signal input to the vibration receiving area.

In some embodiments, the vibration signal may be input to the vibration receiving area by knocking, patting, or scraping in the vibration receiving area.

In some embodiments, the vibration sensing device may be fixedly connected to the solid medium through at least one of bonding, inlaying, welding, riveting, or screw connection.

In some embodiments, the vibration sensing device may be arranged at a position where an amplitude of the solid medium is large.

In some embodiments, the determining, based on the signal feature, an operation of a target object associated with the at least one sensing device may include: determining whether the signal feature meets a predetermined feature; and in response to a determination that the signal feature meets the predetermined feature, determining the operation of the target object corresponding to the predetermined feature.

In some embodiments, the determining whether the signal feature meets a predetermined feature may include: determining, based on a predetermined feature condition identification model, whether the signal feature meets the predetermined feature. The predetermined feature condition identification model may be a machine learning model.

In some embodiments, the operation of the target object may include switching a terminal device from a first state to a second state.

In some embodiments, the obtaining a sensing signal at least one sensing device may include: obtaining a first sensing signal of the at least one sensing device; determining whether the first sensing signal is greater than a signal threshold; and in response to a determination that the first sensing signal is greater than the signal threshold, designating a signal that an interval between the signal and the first sensing signal is within a range of a threshold time as the sensing signal.

In some embodiments, the vibration sensing device may be arranged on a wearable device. The wearable device may be attached to a body part of a user, and the vibration sensing device may receive a vibration signal generated by a body activity of the user through the wearable device.

In some embodiments, the vibration sensing device may be attached to a body part of a user, and the vibration sensing device may receive the vibration signal generated by the body activity of the user.

In some embodiments, the body activity may include coughing, sneezing, snoring, yawning, or falling.

In some embodiments, the determining, based on the signal feature, an operation of a target object associated with the at least one sensing device may include: determining, based on the signal feature, a physiological status of the user; and determining, based on the physiological status of the user, the operation of the target object corresponding to the physiological status.

In some embodiments, the determining, based on the signal feature, a physiological status of the user may include: determining whether the signal feature meets a predetermined feature; and in response to the determination that the signal feature meets the predetermined feature, determining the physiological status corresponding to the predetermined feature.

In some embodiments, the operation of the target object may include a mobile terminal recording a health status or issuing a warning.

In some embodiments, a response frequency of the vibration sensing device may be 2K Hz-4.5K Hz.

In some embodiments, a sensitivity of the vibration sensing device may be $(-35)$ $dBV/(m/s^2)$-$(-15)$ $dBV/(m/s^2)$.

In some embodiments, the at least one sensing device may further include a motion sensing device.

In some embodiments, the determining, based on the signal feature, an operation of a target object associated with the at least one sensing device may include: determining, based on the signal feature, whether the user falls and a body posture of the user; and determining, based on the determining whether the user falls and the body posture of the user, the operation of the target object.

In some embodiments, the determining, based on the determining whether the user falls and the body posture of the user, the operation of the target object may include: in response to a determination that the user falls and the body posture stands still, determining that the user is in a dangerous state, and the mobile terminal performs an operation of calling for help.

In some embodiments, the at least one sensing device may further include a physiological parameter sensing device.

In some embodiments, the determining, based on the signal feature, an operation of a target object associated with the at least one sensing device may include: determining, based on the signal feature, whether the user falls, and the body posture of the user, and at least one physiological parameter; and determining, based on the determining whether the user falls, the body posture of the user, and the at least one physiological parameter, the operation of the target object.

In some embodiments, the determining, based on a determination that whether the user falls, the body posture of the user, and the physiological parameter, the operation of the target object may include: in response to a determination that the user falls, and the body posture stands still or a physiological parameter exceeds a predetermined threshold, determining that the user is in a dangerous state, and the mobile terminal performs the operation of calling for help.

In some embodiments, the physiological parameter may include at least one of a heart rate, a blood pressure, or a blood glucose.

In some embodiments, the body activity may include a tooth tapping.

In some embodiments, the at least one sensing device may include the vibration sensing device arranged at a specific location.

In some embodiments, the identifying a signal feature of the sensing signals may include: identifying the count of vibration peaks, the time interval between two adjacent vibration peaks, and the signal duration of the sensing signal.

In some embodiments, the at least one sensing device may include vibration sensing devices respectively arranged at different positions.

In some embodiments, the signal feature may further include a phase difference of the sensing signals of vibration sensing devices at the different positions, and the phase difference of the sensing signals may be configured to determine a position of a vibration signal.

In some embodiments, the identifying signal features of the sensing signal may include: identifying the count of vibration peaks, the time interval between two adjacent vibration peaks, the signal duration, and the phase difference of the vibration signals.

In some embodiments, the operation of the target object may include switching the terminal device from a first state to a second state.

In some embodiments, the obtaining a sensing signal of at least one sensing device may include: obtaining a second sensing signal of the at least one sensing device; determining whether a frequency of the second sensing signal is lower than a predetermined frequency threshold; and in response to a determination that the frequency of the second sensing signal is lower than the frequency threshold, designating the second sensing signal as a false trigger signal.

In some embodiments, the at least one sensing device may include an audio input device, and the obtaining a sensing signal of at least one sensing device may include: obtaining a third sensing signal of the at least one sensing device; determining whether the audio input device receives user audio information simultaneously; and in response to a determination that the audio input device receives user audio information, designating the third sensing signal as the false trigger signal.

In some embodiments, the obtaining a sensing signal of at least one sensing device may include: obtaining a fourth sensing signal of the at least one sensing device; determining, based on a false trigger identification model, whether the fourth sensing signal is the false trigger signal; and in response to a determination that the fourth sensing signal is not the false trigger signal, designating a signal that an interval between the signal and the fourth sensing signal is within a range of another threshold as the sensing signal.

In some embodiments, the false trigger identification model may be a machine learning model.

Some of the embodiments of the present disclosure further provide a method. The method may include: obtaining a sensing signal of at least one sensing device; identifying a signal feature of the sensing signal; and determining, based on the signal feature, an operation of a target object associated with the at least one sensing device.

Some of the embodiments of the present disclosure further provide a non-transitory computer-readable medium, including: at least one of computer instructions. When executed by at least one processor, the at least one set of computer instructions may direct the at least one processor to perform operations including: obtaining a sensing signal of at least one sensing device; identifying a signal feature of the sensing signal; and determining, based on the signal feature, an operation of a target object associated with the at least one sensing device.

BRIEF DESCRIPTION OF THE DRAWINGS

The present disclosure is further illustrated in terms of exemplary embodiments, and these exemplary embodiments are described in detail with reference to the drawings. These embodiments are not restrictive. In these embodiments, the same number indicates the same structure, wherein.

DETAILED DESCRIPTION

Figure 1:
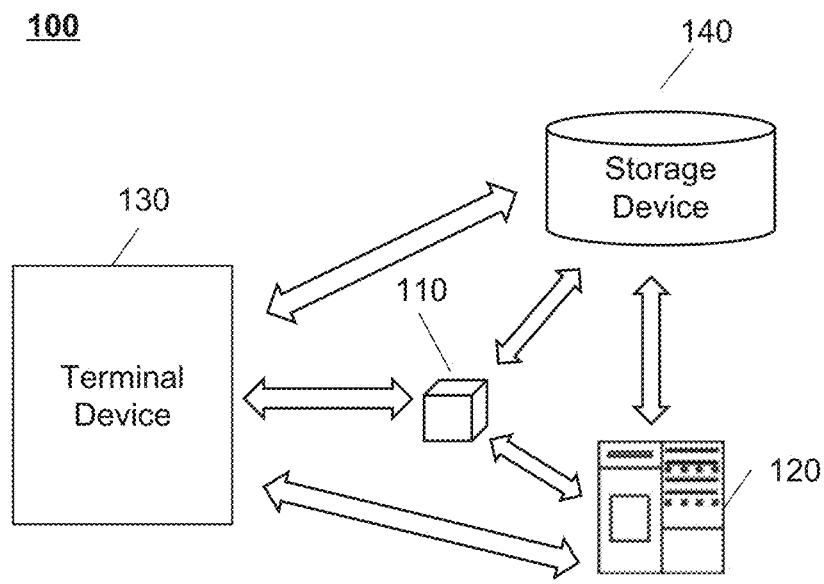
FIG. 1 is a schematic diagram illustrating an exemplary application scenario of a system for controlling target object according to some embodiments in the present disclosure.

In order to illustrate the technical solutions related to the embodiments of the present disclosure, brief introduction of the drawings referred to in the description of the embodiments is provided below. Obviously, drawings described below are only some examples or embodiments of the present disclosure. Those having ordinary skills in the art, without further creative efforts, may apply the present disclosure to other similar scenarios according to these drawings. Unless stated otherwise or obvious from the context, the same reference numeral in the drawings refers to the same structure and operation.

As used in the disclosure and the appended claims, the singular forms "a," "an," and "the" include plural referents unless the content clearly dictates otherwise. In general, the terms "comprise," "comprises," and/or "comprising," "include," "includes," and/or "including," merely prompt to include steps and elements that have been clearly identified, and these steps and elements do not constitute an exclusive listing. The methods or devices may also include other steps or elements. The term "based on" is "based at least in part on." The term "one embodiment" represents "at least one embodiment." The term "another embodiment" represents "at least one other embodiment." Related definitions of other terms will be given in the description below.

Some embodiments of the present disclosure provide a method for determining an operation of a target object. The method may include obtaining a sensing signal by at least one sensing device. The sensing signal may be generated by the sensing device after obtaining an external signal. In some embodiments, the external signal may include a vibration signal, other types of signals, or any combination thereof. Other types of signals may include an acoustic signal, an optical signal, an electrical signal, or the like. Since a vibration signal is transmitted through a solid medium, even in an environment with sound interference or even high noise, the vibration signal may still be accurately and effectively collected by the sensing device. By identifying a signal feature of the sensing signal, an operation of a target object associated with the at least one sensing device may be determined based on the signal feature, so that the operation of the target object may be more accurate and convenient. The target object may refer to a terminal device that is connected/communicated with a sensing device to perform various functions.

FIG. 1 is a schematic diagram illustrating an exemplary application scenario of a system for controlling target object according to some embodiments in the present disclosure. For the convenience of illustration, a system 100 for controlling target object may be referred to as a system 100 for short. The system 100 may include a sensing device 110, a processing device 120, a terminal device 130 (or referred to as a target object), and a storage device 140. In some embodiments, the system 100 may identify a signal feature of a sensing signal collected by the sensing device 110, and determine an operation to be performed by the terminal device based on the signal feature. Each component in the system 100 may be connected to each other in a wired or wireless way.

In some embodiments, a wired connection may include, but not limited to, using a metal cable, an optical cable, or any combination thereof, such as a coaxial cable, a communication cable, a flexible cable, a spiral cable, a non-metal sheathed cable, a metal sheathed cable, a multi-core cable, a twisted-pair cable, a ribbon cable, a shielded cable, a telecommunication cable, a duplex cable, a twin-lead cable, and a twisted pair. The examples described above are merely for the convenience of illustration. A medium of the wired connection may also be other types, such as a transmission carrier of other electrical signals or optical signals.

A wireless connection may include, but not limited to, a radio communication, a free space optical communication, an acoustic communication, an electromagnetic induction, or the like. The radio communication may include, but not limited to, an IEEE302.11 series standard, an IEEE302.15 series standard (e.g., a Bluetooth technology and a Zigbee technology, etc.), a first-generation mobile communication technology, a second-generation mobile communication technology (e.g., frequency division multiple access (FDMA), a time division multiple access (TDMA), space division multiple access (SDMA), code division multiple access (CDMA), spread spectrum multiple access (SSMA), etc.), a general packet radio service technology, a third-generation mobile communication technology (e.g., CDMA2000, a wideband code division multiple access (WCDMA), time division-synchronous code division multiple access (TD-SCDMA), world interoperability for microwave access (WIMAX), etc.), a fourth-generation mobile communication technology (e.g., a TD-SCDMA long term evolution (TD-LTE), frequency-division duplex long term evolution (FDD-LTE), etc.), a satellite communication (e.g., a global positioning system (GPS) technology, etc.), a near-field communication (NFC), and other technologies operating in an industrial scientific medical (ISM) band (e.g., 2.4 GHz, etc.). The free space optical communication may include but not limited to a visible light, an infrared signal, etc. The acoustic communication may include but not limited to a sound wave, an ultrasonic signal, etc. The electromagnetic induction may include but not limited to a near-field communication technology. The examples described above are merely for the convenience of illustration. A medium of wireless connection may also be other types, such as a Z-wave technology, other chargeable civil radio bands, military radio bands, or the like.

The sensing device 110 may collect an external signal and generate a sensing signal based on the external signal (e.g., an electrical signal). The external signal may include a mechanical vibration signal (which may also be referred to as a vibration signal), an acoustic signal, an optical signal, an electrical signal, or the like. In some embodiments, the external signal may be derived from a user or input by a user through a specific way, which may also be referred to as a user signal. The sensing device 110 may include, but not limited to a pressure sensing device, a vibration sensing device, a tactile sensing device, an audio input device, an optical sensing device, or the like, or any combination thereof. In some embodiments, the sensing device 110 may include at least a vibration sensing device to collect a vibration signal. In some embodiments, a user may input a signal to the sensing device 110 to cause the sensing device to generate a corresponding sensing signal. For example, the sensing signal 110 may collect a vibration signal input a user (e.g., by a door panel knocking, a tooth tapping, etc.). Since the vibration signal is hardly affected by environmental noise during transmission, the vibration signal may be accurately and effectively collected by the sensing device 110.

The processing device 120 may process data and/or information obtained from other components from the sensing device 110, the storage device 140 or the system 100. For example, the processing device 120 may process a sensing signal obtained from the sensing device 110 and determine a signal feature of the sensing signal. In some embodiments, the processing device 120 may be an independent server or a server group. The server group may be centralized or distributed. In some embodiments, the processing device 120 may be local or remote. For example, the processing device 120 may access information and/or data from the sensing device 110, the terminal device 130 and/or the storage device 140. As another example, the processing device 120 may be directly connected to the sensing device 110, the terminal device 130 and/or the storage device 140 to access information and/or data. In some embodiments, the processing device 120 may include one or more sub-processors (e.g., single-core processor(s) or multi-core processor(s)). Merely by way of example, the processor may include a central processing unit (CPU), an application-specific integrated circuit (ASIC), an application-specific instruction-set processor (ASIP), a graphics processing unit (GPU), a physics processing unit (PPU), a digital signal processor (DSP), a field-programmable gate array (FPGA), a programmable logic device (PLD), a controller, a micro-controller unit, a reduced instruction-set computer (RISC), a microprocessor, or the like, or any combination thereof. In some embodiments, the processing device 120 may be a chip. The chip may be arranged in the sensing device 110. In some specific embodiments, the processing device 120 may be a processor of the sensing device 110 thereof (e.g., a chip of the sensing device 110), which may not only pick up and collect a vibration signal, but also process a sensing signal generated by the sensing device 110.

The storage device 140 may store data, instructions, and/or any other information, such as the sensing signal, signal feature information of the sensing signal. In some embodiments, the storage device 140 may store data obtained from the sensing device 110 and/or the processing device 120. In some embodiments, the storage device 140 may store data and/or instructions that the processing device 120 may execute or use to perform exemplary methods described in the present disclosure. In some embodiments, the storage device 140 may include a mass storage device, a removable storage device, a volatile read-write memory, a read-only memory (ROM), or the like, or any combination thereof. In some embodiments, the storage device 140 may be implemented on a cloud platform.

In some embodiments, the storage device 140 may be in communication with at least one other component in the system 100 (e.g., the processing device 120). The at least one component in the system 100 may access data stored in the storage device 140 (e.g., a signal feature). In some embodiments, the storage device 140 may be a portion of the processing device 120.

In some embodiments, the terminal device 130 may include a mobile device, a tablet computer, a laptop computer, a built-in device in a vehicle, a smart home device, or the like, or any combination thereof. In some embodiments, the mobile device may include a wearable device, a smart mobile device, a virtual reality device, an augmented reality device, a smart toy, a smart speaker, or the like, or any combination thereof. In some embodiments, the wearable device may include a smart bracelet, a smart footgear, a pair of smart glasses, a smart helmet, a smart watch, a smart clothing, a smart backpack, a smart accessory, or the like, or any combination thereof. In some embodiments, the smart mobile device may include a smart phone, a personal digital assistant (PDA), a gaming device, a navigation device, a point of sale (POS) device, or the like, or any combination thereof. In some embodiments, the virtual reality device and/or augmented reality device may include a virtual reality helmet, a pair of virtual reality glasses, a virtual reality patch, an augmented reality helmet, a pair of augmented reality glasses, an augmented reality patch, or the like, or any combination thereof. In some embodiments, the built-in device may include a vehicle-mounted telephones, a vehicle-mounted multimedia, a Bluetooth, a navigation, etc. In some embodiments, the smart home device may include a smart lighting device (e.g., a light), a control device of an intelligent electrical apparatus, a smart monitoring device, a smart television, a smart video camera, an interphone, or the like, or any combination thereof.

Figure 2:
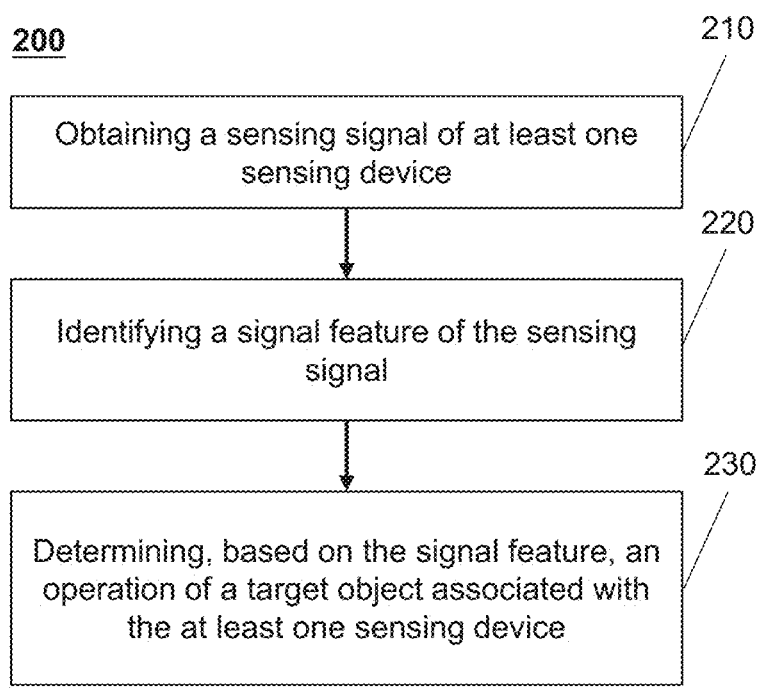
FIG. 2 is a flowchart illustrating an exemplary process for controlling a target object according to some embodiments of the present disclosure.

FIG. 2 is a flowchart illustrating an exemplary process for controlling a target object according to some embodiments of the present disclosure. Specifically, the method 200 for controlling a target object may be executed by the system 100 for controlling a target object (e.g., a processing device 120). For example, the method 200 for controlling a target object may be stored in a storage device (such as a self-contained storage unit of the processing device 120 or the storage device 140) in the form of a program or an instruction. The method 200 for controlling a target object may be implemented when the system 100 for controlling a target object (e.g., the processing device 120) executes the program or the instruction. The operation of the process below is merely for the purpose of illustration. In some embodiments, the process 200 may be accomplished with one or more additional operations not described and/or without one or more of the operations discussed. In addition, an order of operations of the process 200 in FIG. 2 and described below is not restrictive.

In 210, the processing device 120 may obtain a sensing signal of at least one sensing device 110. In some embodiments, the operation 210 may be performed by a sensing signal obtaining module 310.

A sensing signal may refer to a signal generated based on the external signal after the external signal 110 receives an external signal. For example, a sensing signal may be an electrical signal generated by the sensing signal 110 based on a received vibration signal. In some embodiments, the external signal may include a mechanical vibration signal (which may also be referred to as a vibration signal), other types of signals, or any combination thereof. Other types of signals may include an optical signal, an acoustic signal, an electrical signal, or the like. The sensing device 110 may include, but not limited to a vibration sensing device, a pressure sensing device, a tactile sensing device, an audio input device, an optical sensing device, or the like, or any combination thereof. For example, the sensing device 110 may include at least a vibration sensing device to collect a vibration signal. In some embodiments, a vibration signal may be generated by a body activity of a user, a tooth tapping of a user, or by performing a specific operation (e.g., a vibration receiving area) in a specific area (e.g., a knocking, patting, scraping, etc.). The sensing device 110 may receive the vibration signal and generate a corresponding sensing signal based on the vibration signal.

In 220, the processing device 120 may identify a signal feature of the sensing signal. In some embodiments, the operation 220 may be performed by a signal feature identification module 320.

The signal feature may refer to relevant information that reflects signal characteristics. In some embodiments, the processing device 120 may identify the signal feature of the sensing signal by performing time domain processing and/or frequency domain processing on the sensing signal. For a vibration signal, a signal feature of a sensing signal corresponding to the vibration signal may include, but not limited to a count of vibration peaks, a signal strength, a time interval between two adjacent vibration peaks, frequency components, a signal duration, or the like, or any combination thereof.

The count of vibration peaks may refer to a count of vibration peaks whose amplitude is greater than a predetermined amplitude. The count of vibration peaks may reflect a count feature of external signals (e.g., a count of times of user knockings, a count of times of tooth tapping, a count of times of specific body activities, etc.). The signal strength may refer to a strength of a signal. The signal strength may reflect a strength feature of an external signal (e.g., a strength of a user knocking and patting). The stronger the user knocks and taps, the greater the signal strength of the vibration signal generated. The time interval between two adjacent vibration peaks may refer to a time interval between two adjacent vibration peaks in a vibration peak. In some embodiments, the time interval of two adjacent vibration peaks may reflect a density feature of external signals (e.g., a time interval of user knocking, patting, and tooth tapping, a time interval between two adjacent body activities, etc.). The frequency components of a signal may refer to information on a proportion of each frequency in the sensing signal. The proportion information of each frequency may include, for example, a proportion of high-frequency signals, medium-high-frequency signals, medium-frequency signals, medium-low-frequency signals, low-frequency signals, etc. The high frequency, medium-high frequency, medium frequency, medium-low frequency and/or low frequency in the present disclosure may be artificially defined. For example, a high-frequency signal may be a signal with a frequency greater than 4000 Hz. A medium-high-frequency signal may be a signal with a frequency within a range of 2500 Hz-5000 Hz. A medium-frequency signal may be a signal with a frequency within a range of 1000 Hz-4000 Hz. A medium-and-high frequency signal may be a signal with a frequency within a range of 600 Hz-2000 Hz. A low-frequency signal may be a signal with a frequency within a range of 20 Hz-1000 Hz. The signal duration may refer to a duration of an entire sensing signal or a duration of a single vibration peak in a sensing signal. For example, the entire sensing signal may include three vibration peaks, and the duration of the entire sensing signal may be 3 seconds.

In some embodiments, the processing device 120 may determine a signal feature spectrum of a sensing signal by performing time domain processing and/or frequency domain processing on the sensing signal, thereby determining the signal feature of the sensing signal. More descriptions for the signal feature of identifying the sensing signal may refer to the embodiments in FIG. 4, which may not be described herein.

In 230, the processing device 120 may determine, based on the signal feature, an operation of a target object associated with the at least one sensing device 110. In some embodiments, the operation 220 may be performed by an operation determination module 330.

The target object may refer to a terminal device 130 configured to perform a specific function. For example, a mobile device (such as a smartphone, a smart watch, etc.) for making calls. As another example, an audio device configured to play music (such as a headphone, a vehicle-mounted speaker, a Bluetooth speaker, etc.). As yet another example, a lighting device configured to light (such as an indoor bulb, a car light, etc.). It should be noted that the terminal device 130 listed above is merely for example. The terminal device 130 may be any device that performs functions required by a user. The association of the target object with the at least one sensing device 110 may be understood as the terminal device 130 being configured to perform a specific function in response to a specific signal feature of the sensing signal of the sensing device 110. In some embodiments, the target object may be in communication with the processing device 120. In some embodiments, the manner of communication connection may include a wired connection or a wireless connection. For example, the wired connection via a cable. As another example, the wireless connection via a Bluetooth device. The operation of the target object may refer to a function of the terminal device 130, for example, playing/ pausing music, making/hanging up calls, turning on/turning off lighting, or the like. More descriptions for the operation of determining the target object based on the signal feature may refer to the embodiments in FIGS. 4-10, which may not be described herein.

In some embodiments, the processing device 120 may determine, based on the signal feature, a physiological status of the user. Further, the processing device 120 may determine, based on the physiological status of the user, the operation of the target object corresponding to the physiological status. In some embodiments, the processing device 120 may determine, based on the signal feature, whether the user falls and a body posture of the user, and determine, based on the determining whether the user falls and body posture of the user, the operation of the target object. In some embodiments, the processing device 120 may determine, based on the signal feature, whether the user falls, the body posture of the user, and at least one physiological parameter, and determine, based on the determining whether the user's fall, and the body posture of the user, and the at least one physiological parameter, the operation of the target object. More descriptions for determining the physiological status of the user based on the signal feature may refer to the embodiments in FIGS. 11-18, which may not be described herein.

In some embodiments, when the processing device 120 obtains a sensing signal, anti-false trigger processing may be performed. For example, the processing device 120 may obtain a sensing signal of the at least one sensing device 110 in real-time or intermittently. When the processing device 120 obtains the sensing signal (also referred to as a first sensing signal), the processing device 120 may determine whether a signal strength of the first sensing signal is greater than a signal threshold. When the signal strength of the first sensing signal is less than the signal threshold, the processing device 120 may designate the first sensing signal as a false trigger signal. When the signal strength of the first sensing signal is greater than the signal threshold, the processing device 120 may designate a signal that an interval between the signal and the first sensing signal threshold is within a range of a threshold time as the sensing signal. More description for the sensing signal of the at least one sensing device 110 may be found elsewhere in the present disclosure, which may not be described herein.

Figure 3:
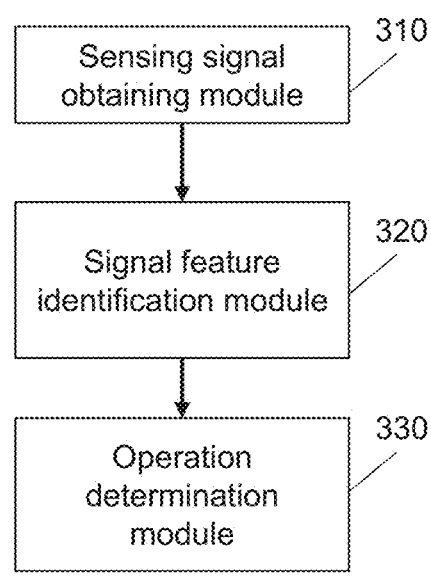
FIG. 3 is a block diagram illustrating an exemplary system for controlling a target object according to some embodiments of the present disclosure.

FIG. 3 is a block diagram illustrating an exemplary system for controlling a target object according to some embodiments of the present disclosure. As shown in FIG. 3, the system 300 for controlling a target object may include a sensing signal obtaining module 310, a signal feature identification module 320, and an operation determination module 330. In some embodiments, the system 300 for controlling a target object may be implemented by the system 100 for controlling a target object (e.g., the processing device 120) shown in FIG. 1.

In some embodiments, the sensing signal obtaining module 310 may be configured to obtain a sensing signal of a vibration sensing device. In some embodiments, the sensing signal obtaining module 310 may also be configured to obtain a sensing signal of at least one sensing device 110.

In some embodiments, the signal feature identification module 320 may be configured to identify a signal feature of a vibration sensing signal. In some embodiments, the signal feature identification module 320 may also be configured to identify a signal feature of the sensing signal.

In some embodiments, the operation determination module 330 may be configured to determine, based on the signal feature, an operation of a target object associated with the at least one sensing device 110. In some embodiments, the operation determination module 330 may also be configured to determine, based on the signal feature, a physiological status of the user. In some embodiments, the operation determination module 330 may also be configured to determine, based on the physiological status of the user, the operation of the target object associated with the at least one sensing device 110.

It should be noted that the above description of the system 300 for controlling a target object and the devices/modules thereof are merely provided for the convenience of description, and not intended to limit the scope of the present disclosure. It will be understood that for those skilled in the art, after understanding the principle of the system, it is possible to arbitrarily combine various components, or form subsystems to connect with other components without departing from this principle. For example, the signal feature identification module 320 and the operation determination module 330 shown in FIG. 3 may be different modules embodied in a device (e.g., the processing device 120), or one module that may implement functions of the above two or two modules. As another example, each module may have its own storage module. As yet another example, each module may share a storage module. Those variations are still within the scope of the present disclosure.

Figure 4:
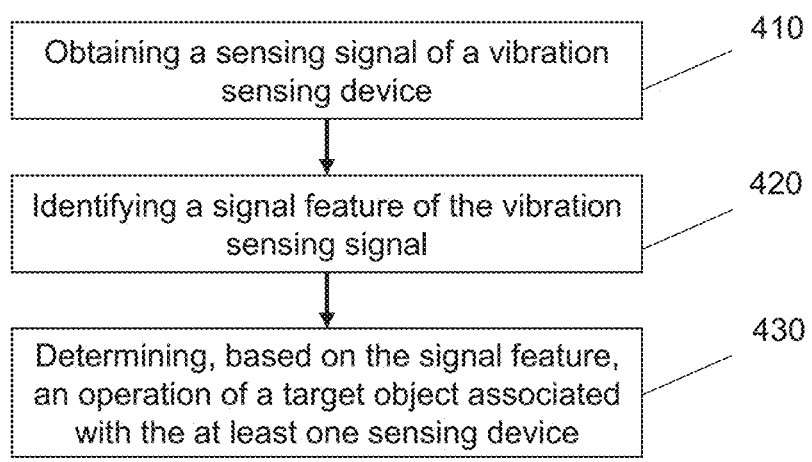
FIG. 4 is a flowchart illustrating an exemplary process for controlling a target object according to some embodiments of the present disclosure.
Figures 5A, 5B, 5C, 5D:
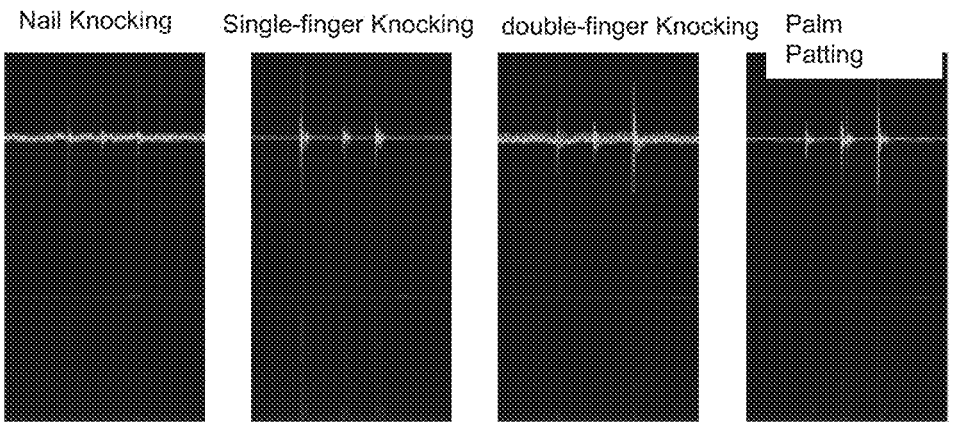
FIGS. 5A-5D are schematic diagrams illustrating signal feature spectra of vibration signals generated by different operations of a user according to some embodiments of the present disclosure.

FIG. 4 is a flowchart illustrating an exemplary process for controlling a target object according to some embodiments of the present disclosure. Specifically, the method 400 for controlling a target object may be performed by the system 100 for controlling a target object (e.g., the processing device 120). For example, the method 400 for controlling a target object may be stored in a storage device (such as a self-contained storage unit of the processing device 120 or the storage device 140) in the form of a program or an instruction. The method 400 for controlling a target object may be implemented when the system 100 for controlling a target object (e.g., the processing device 120) executes the program or the instruction. The operation of the process below is merely for the purpose of illustration. In some embodiments, the process 400 may be accomplished with one or more additional operations not described and/or without one or more of the operations discussed. In addition, an order of the operations of the process 400 in FIG. 4 and described below is not restrictive. In some embodiments, the process 400 may be applied to fields of a smart home, a smart car, a smart factory, a smart speaker, a smart toy, or the like.

In 410, the processing device 120 may obtain a sensing signal of a vibration sensing device. In some embodiments, the operation 410 may be performed by a sensing signal obtaining module 310.

The vibration sensing device may collect a vibration signal. For example, the vibration sensing device may be a microphone (also referred to as a bone conduction microphone), an acceleration meter, etc. with bone conduction as one of main sound transmission manners. In some embodiments, the vibration sensing device may collect a vibration signal in a specific area. The specific area may be an artificially set area for receiving vibration signals, or may also be referred to as a vibration receiving area. In some embodiments, the vibration sensing device may obtain the vibration signal of the vibration receiving area and generate a corresponding sensing signal. The sensing signal generated by obtaining the vibration signal may be also called a vibration sensing signal. The vibration sensing signal may be, for example, an electrical signal.

In some embodiments, the vibration sensing device may include a housing. The housing may have a certain hardness to facilitate transmission of the vibration signal. For example, the housing of the vibration sensing device may be used as a vibration receiving area. A user may perform a specific operation on the housing (e.g., knocking, patting, scrapping, or the like, or any combination thereof) to generate a specific vibration signal. This specific vibration signal may correspond to a specific operation instruction.

Due to small loss of mechanical vibration in a solid, the vibration receiving area may not need to be arranged at a position of the vibration sensing device (e.g., the housing of the vibration sensing device). In some embodiments, the vibration receiving area may be arranged at a position where mechanical vibration may be effectively transmitted. In some embodiments, the vibration receiving area may be provided on a solid medium. The solid medium may be metal (e.g., stainless steel, aluminum alloy, etc.), non-metal (e.g., wood, plastic, etc.), etc. The vibration sensing device may be connected to the vibration receiving area through the solid medium, and receive the vibration signal input into the vibration receiving area. The vibration signal received by the vibration receiving area may be transmitted to the vibration sensing device through the solid medium. In some embodiments, the vibration receiving area may be a selected area in the solid medium. For example, in the embodiments shown in FIG. 6, the vibration sensing device may be arranged on a door 610 and/or a headboard 630. As another example, in the embodiment shown in FIG. 8, the vibration sensing device may be arranged on a steering wheel 820.

In some embodiments, the vibration sensing device may be fixedly connected to the solid medium. A manner of fixed connection may include, but not limited to bonding, inlaying, welding, riveting, screw connection, buckle connection, etc. to ensure that the vibration sensing device has good and firm contact with the solid medium, so that the vibration signal may be accurately and effectively transmitted from the solid medium to the vibration sensing device. For example, in the embodiments shown in FIG. 6, at least one vibration sensing device may be bonded to the door 610, or at least one vibration sensing device may be bonded to the headboard 630 or connected to a side wall by screws. As another example, in the embodiments shown in FIG. 8, at least one vibration sensing device may be inlaid in the steering wheel 820. In some specific embodiments, the vibration sensing device may be connected to the solid medium by means of bonding, which may be not only convenient and quick to connect, but also easy to disassemble. In some cases, the vibration sensing device may be inlaid in or bonded to the solid medium (e.g., the door 610 and the side wall in an indoor environment 600, a steering wheel 820 in a usage environment 800, etc.). Due to small loss of mechanical vibration transmitted in the solid medium, the signal strength may be still large enough when a distance is long, so a signal input area (that is, the vibration receiving area) may be effectively expanded. The vibration signal may be input within a wide range, which may save the user a trouble of finding an operation panel or button, and improve the user experience. In some cases, especially in a dark environment, the user may be prevented from moving around in order to control a light 640 (e.g., in the indoor environment 600, in order to find a switch of the light 640, the user may need to walk to a position where the switch is set on the side wall), bumping into a table and chairs, etc.

In some embodiments, the vibration sensing device may be arranged at any portion of the solid medium. Taking the door 610 shown in FIG. 6 as an example, an exemplary installation position may include a door frame of the door 610, a door handle of the door 610, a bottom of the door 610, a center of the door 610, etc. In some embodiments, the vibration sensing device may be arranged at a position with a large vibration amplitude on the solid medium. For example, when the user knocks on the door 610, the amplitude near the center of the door 610 may be usually large, and the vibration signal received by the vibration sensing device may be stronger.

For example, the vibration sensing device may be bonded to the door 610, and an upper half area of the door 610 may serve as a vibration receiving area. The user may perform specific operations in the upper half area of the door 610 (that is, the vibration receiving area), and the generated vibration signal may be transmitted to the vibration sensing device connected with the door 610 via the door 610.

In some embodiments, the vibration receiving area may be at least a portion of the solid medium. In some embodiments, the vibration receiving area may be located where the user is easy to operate (e.g., knocking, patting, or scraping). For example, in the indoor environment 600 shown in FIG. 6, the solid medium may be a door 610, and the vibration receiving area may be a surface of the door 610 away from the indoor environment 600. As another example, in the indoor environment 600, the upper half area of the door 610 may serve as a vibration receiving area. In some embodiments, the vibration receiving area may have any location, shape and/or size. For example, the solid medium may be the headboard 630, and the vibration receiving area may be 630 headboard or a specific area thereon (e.g., a right side, a left area of the headboard 630, etc.). As another example, when the solid medium is the headboard 630, an entire surface of the headboard 630 facing the user may serve as a vibration receiving area.

In some embodiments, the vibration receiving area may also be an independent structure arranged on the solid medium. For example, the vibration receiving area may be a vibration receiving surface arranged on a surface of the door 610. The vibration receiving surface may be a rigid sheet-like object or a plate-like object, for example, an iron sheet, a steel plate, or the like. In some embodiments, the vibration receiving surface may be detachably connected to the solid medium. In some embodiments, the vibration receiving surface may be installed in any position of the solid medium according to needs of the user. For example, in the embodiments shown in FIG. 6, the user is usually located in the right area of the bed 620, so the vibration receiving surface may be arranged in the right area of the headboard 630.

In addition, in some embodiments, the vibration receiving area may also be a portion of the vibration sensing device. The housing of the vibration sensing device described in the above-mentioned embodiments may serve as the vibration receiving area.

In order to prevent the user from being injured when performing a specific operation to input a vibration signal, in some embodiments, an outer package of the vibration sensing device (e.g., an outer housing of the sensing device) and/or the vibration receiving area need to avoid sharp edges and corners. For example, the outer package surface of the vibration sensing device may be set to a circular arc surface. In some embodiments, an installation position of the vibration sensing device may avoid a position where the user often performs specific operations. For example, a user sleeping on a right side of the bed 620 usually knocks, taps, and/or scrap a right edge of the headboard 630, so the vibration sensing device may be inlaid inside the headboard 630 or the vibration sensing device may be arranged at a position away from the right side of the headboard 630 (e.g., a top area, a right area, etc. of the headboard 630) so that the user will not touch the outer package of the vibration sensing device when performing a specific operation.

In some embodiments, the vibration sensing device may be powered by a battery arranged inside. Exemplary types of battery may include a lithium battery, a hydrogen fuel cell, an alkaline zinc manganese battery, a nickel cadmium battery, a nickel hydrogen battery, etc. In some embodiments, the vibration sensing device may be powered by an external power supply. For example, the vibration sensing device may be connected to an external power supply by using a power cord or a wireless charging module, so as to be powered by the external power supply. The external power supply may be, for example, a portable charger, household electricity, etc.

The vibration sensing device may have a certain volume. In some embodiments, the volume of the vibration sensing device may be between 1 mm$^3$ and 10 cm$^3$. In some embodiments, the volume of the vibration sensing device may be between 0.5 mm$^3$ and 20 cm$^3$. In some embodiments, the volume of the vibration sensing device may be between 1.5 mm$^3$ and 5 cm$^3$. In some embodiments, the volume of the vibration sensing device may be between 2 mm$^3$~1 cm$^3$.

In some embodiments, in order to enable the vibration sensing device to completely and clearly collected the vibration signal input by the user, a certain requirement may be also required for a sensitivity of the vibration sensing device. The sensitivity may be understood as a size of a response of the sensing device to a specific signal during the operation. In some embodiments, the sensitivity of the vibration sensing device may be $(-50)$ dBV/(m/s$^2$)~$(-10)$ dBV/(m/s$^2$). In some embodiments, the sensitivity of the vibration sensing device may be $(-35)$ dBV/(m/s$^2$)~$(-15)$ dBV/(m/s$^2$). In some embodiments, the sensitivity of the vibration sensing device may be $(-30)$ dBV/(m/s$^2$)~$(-15)$ dBV/(m/s$^2$). In some embodiments, the sensitivity of the vibration sensing device may be $(-25)$ dBV/(m/s$^2$)~$(-20)$ dBV/(m/s$^2$).

In 420, the processing device 120 may identify a signal feature of the vibration sensing signal. In some embodiments, the operation 420 may be performed by a signal feature identification module 320.

In some embodiments, the processing device 120 may process the vibration sensing signal (e.g., time domain processing and/or frequency domain processing, etc.), and output the vibration sensing signal as a signal feature spectrum. Based on the signal feature spectrum, the processing device 120 may identify the signal feature of the sensing signal. For example, the processing device 120 may read relevant information such as a count of vibration peaks, frequency components of a signal, etc. from the signal feature spectrum. In some embodiments, the processing device 120 may also directly identify the signal feature based on the relevant data/information of the vibration signal collected the vibration sensing device. For example, the processing device 120 may calculate a time interval between two adjacent vibration peaks according to a time at which the two vibration peaks are obtained.

In some embodiments, the processing device 120 may identify at least one signal feature of the sensing signal, such as a count of vibration peaks, a signal strength, a time interval between two adjacent vibration peaks, frequency components, a signal duration, or the like, or any combination thereof. For example, the processing device 120 may identify the signal feature of the sensing signal as three vibration peaks. As another example, the processing device 120 may simultaneously identify the count of vibration peaks and the time interval between two adjacent vibration peaks. For example, the processing device 120 may identify that the signal feature of a sensing signal is that there are three vibration peaks within 2 s. A time interval between two previous vibration peaks may be short (e.g., 0.1 s, 0.2 s, 0.3 s, 0.4 s, 0.5 s, etc.). A time interval between two following vibration peaks may be long (e.g., 1.1 s, 1.2 s, 1.3, 1.4 s, 1.5 s, etc.). As another example, the processing device 120 may simultaneously identify the frequency components, the signal strength, and the signal duration of the sensing signal. For example, the processing device 120 may identify that the signal feature of the sensing signal is that there are many components of medium-frequency and high-frequency signals (e.g., medium-frequency and high-frequency signals account for more than 70%), the vibration amplitude (that is, the signal strength) is small, and the signal duration is short (e.g., the signal only lasts for 1 second), and the generated vibration peak is relatively sharp.

In some embodiments, the processing device 120 may identify the signal feature of the vibration sensing signal based on a feature extraction model. The processing device 120 may input the sensing signal into the feature extraction model. Output of the feature extraction model may include at least one signal feature of the vibration sensing signal, such as a count of vibration peaks, a signal strength, a time interval between two adjacent vibration peaks, frequency components, a signal duration, or the like, or any combination thereof. In some embodiments, the feature extraction model may be a machine learning model. The feature extraction model may be a trained machine learning model. This machine learning model may include various models and structures, such as a deep neural network model, a recurrent neural network model, a custom model structure, etc. which may not be limited in the present disclosure.

In some embodiments, when training a feature extraction model, a plurality of vibration sensing signals with labels (or identifiers) may be used as training data. Parameters of the model may be learned through common ways such as gradient decline. In some embodiments, the feature extraction model may be trained in other devices or modules.

In 430, the processing device 120 may determine, based on the signal feature, an operation of a target object associated with the at least one sensing device 110. In some embodiments, the operation 430 may be performed by an operation determination module 330.

In some embodiments, the processing device 120 may further determine an operation instruction configured to control the target object to perform an operation. The operation instruction may instruct the target object (e.g., a terminal device 130) to perform an operation. For example, in the embodiment shown in FIG. 6, the operation instruction may instruct a light 640 to be turned on or turned off. In the embodiment, the user may generate a specific vibration signal by performing a specific action. The vibration sensing device may collect these vibration signals and generate corresponding sensing signals for processing by a processing device 120. The processing device 120 may determine an operation of the target object, thereby achieving control of the target object. Compared with voice interaction, noise in an environment may have little influence on the vibration signal. Even in a high-noise environment, the vibration signal may still be completely and effectively collected by the vibration sensing device, which may make the operation or the operation instruction of the target object determined by the signal processing device 120 more accurate.

In some embodiments, the processing device 120 may determine whether the identified signal feature meets at least one of a plurality of predetermined features. The predetermined feature condition may include one predetermined feature, a plurality of predetermined features, or any combination thereof. In some embodiments, the processing device 120 may use a signal feature corresponding to a specific operation of the target object as a predetermined feature condition. In some embodiments, each predetermined feature condition may correspond to a specific operation of the target object and/or an instruction configured to control the target object to perform a specific operation. For example, the predetermined feature condition may be that three vibration peaks appear within 1 s, and a time interval between two adjacent vibration peaks is equal or similar (e.g., a difference is within a threshold range of 0.3 s, 0.5 s, 0.8 s, etc.). The predetermined feature condition may indicate that the user knocks or taps a vibration receiving area 3 times at the same or similar time interval within 1 s. As another example, three vibration peaks may appear within 2 s (indicating that the user knocks and taps 3 times within 3 s). A time interval between two previous vibration peaks may be short (e.g., 0.5 s), and a time interval between two following vibration peaks may be long (e.g., 2 s), or a time interval between two previous vibration peaks may be long (e.g., 2 s), and a time interval between two following vibration peaks may be short (e.g., 0.5 s). Each predetermined feature condition may correspond to different operations or operation instructions of the target object. For example, the predetermined feature condition may be that the operation instruction corresponding to two vibration peaks within 1 s is to turn on or turn off a light (e.g., the light 640 in FIG. 6). As another example, the predetermined feature condition may be that three vibration peaks appear within 3 s. A time interval between two previous vibration peaks may be short. A time interval between two following vibration peaks may be long, and a corresponding operation instruction may be to make the light 640 into a warm light mode. The predetermined feature condition may be that three vibration peaks appear within 3 s. A time interval between two previous vibration peaks may be longer. A time interval between two following vibration peaks may be short, and a corresponding operation instruction may be to make the light 640 into a cold light mode.

In some embodiments, the user may also set a predetermined feature condition and an operation or an operation instruction corresponding to a corresponding target according to needs of the user. For example, the user may set a predetermined feature condition corresponding to a commonly used operation as a simplified predetermined feature condition (e.g., including few signal features), which may be easier to achieve. For example, the user may set the predetermined feature condition corresponding to an operation of turning on the light 640 to have two vibration peaks within 1 s, so that the light 640 may be turned on quickly every time the user enter an indoor environment 600.

In some embodiments, the predetermined feature may include only one signal feature, which may be convenient for the user to memorize and operate. In some embodiments, the predetermined feature condition may be a combination of a plurality of signal features, so as to achieve more complicated control and avoid a false operation simultaneously through a combination of different signal features. In some specific embodiments, the predetermined feature condition may include a signal strength and a count of vibration peaks. For example, two vibration peaks may appear within 1 s. A peak value of a previous vibration peak may be small, and a peak value of a following vibration peak may be large, or a peak value of a previous vibration peak may be large, and a peak value of a following vibration peak may be small, which may respectively correspond to two different operation instructions.

In some specific embodiments, when the user knocks on and taps a solid medium at different parts, different vibration signals may be generated in the solid medium (e.g., vibration signals with different frequency components, durations, and/or signal strengths). Correspondingly, the vibration sensing signal generated by the vibration sensing device may be also different (e.g., vibration sensing signals with different frequency components, durations, and/or signal strengths). At this time, frequency components, a duration, and/or a signal strength may be combined to form more predetermined feature conditions, corresponding to more complicated operations.

FIGS. 5A-5D are schematic diagrams illustrating signal feature spectra of vibration signals generated by different operations of a user according to some embodiments of the present disclosure. FIGS. 5A-5D sequentially show signal feature spectra of vibration sensing signals generated by nail knocking, single-finger knocking, multi-finger knocking, and palm patting. As shown in FIGS. 5A-5D, vibration sensing signals corresponding to the nail knocking, the single-finger knocking, the multi-finger knocking, and the palm-patting are different. For example, the nail texture may be relatively hard, so that a sensing signal may have many medium-frequency signal and high-frequency signal components. A vibration amplitude may be generally small, a duration of a single vibration peak may be short, and a generated vibration peak may be relatively sharp. As another example, the force of the single-finger knocking may be generally greater than that of the nail knocking, and due to the buffering of the skin tissue, low-frequency or medium-low-frequency signal components may be increased in the sensing signal, and a signal duration may also increase. As yet another example, during the multi-finger knocking, a plurality of knuckles may not touch a surface of the solid medium simultaneously, so a plurality of vibration peaks that are close to each other may be generated. As yet another example, the muscle tissue on the palm may be more than the knuckles, there may be a larger buffer when patting, and there may be a larger contact area with the surface of the solid medium, resulting in more medium-frequency and low-frequency signal components in the vibration signal generated by palm patting, and a relatively long signal duration. In some embodiments, the user may also pat, knock, and scrap with different tools to generate vibration sensing signals with different signal features, corresponding to more operating instructions to achieve more complicated control. For example, when the solid medium is tapped with objects such as a key, a mobile phone, a water cup, a glove, etc., a vibration signal with different signal features may be generated. In some cases, the user may use different tools to achieve more complex device control while avoiding false triggering. For example, in the indoor environment 600 shown in FIG. 6, the user may use a key to knock the door 610 three times within 1 s to turn off or turn on the light 640. The light 640 may enter into a warm light mode by knocking the door 610 three times within 1 s with a finger, which may effectively avoid a false operation.

In some embodiments, the processing device 120 may determine whether the signal feature meets a predetermined feature condition based on a difference between the signal feature of the sensing signal and the predetermined feature condition. For example, the predetermined feature condition may be that two vibration peaks may appear within 1 s, and a strength of a second vibration peak may be lower than a strength of a first vibration peak (that is, 2 times within 1 s. A previous knocking may be heavy, and a following knocking may be light) The processing device 120 may determine a count of vibration peaks that appear in a collected sensing signal within 1 s. If the count of vibration peaks is not 2, it may be determined that the signal feature does not meet the predetermined feature condition. If the count of vibration peaks is 2, the processing device 120 may continue to determine strengths of two vibration peaks of the sensing signal, and determine whether the signal strength of the second vibration peak is lower than the signal strength of the first vibration peak. It may be determined that the signal feature does not meet the predetermined feature condition in response to a determination that the signal strength of the second vibration peak is not lower than that of the first vibration peak. It may be determined that the signal feature meets the predetermined feature condition in response to a determination that the signal strength of the second vibration peak is lower than that of the first vibration peak.

In some embodiments, the processing device 120 may determine whether the signal feature meets a predetermined feature condition based on a signal feature spectrum of the sensing signal and a signal feature spectrum of the predetermined feature condition. For example, the processing device 120 may compare the signal feature spectrum of the sensing signal with the signal feature spectrum of the predetermined feature condition. If signal curves in the two signal feature spectra overlap or are similar, it may be determined that the signal feature meets the predetermined feature condition.

In some embodiments, the processing device 120 may determine whether the signal feature meets the predetermined feature condition based on a predetermined feature condition identification model. When the signal feature meets the predetermined feature condition, the processing device 120 may determine an operation or an operation instruction corresponding to the signal feature.

In some embodiments, the predetermined feature condition identification model may be a machine learning model. In some embodiments, the processing device 120 may use the signal feature spectrum of the sensing signal collected by the vibration sensing device as input data of the machine learning model. A result that whether the signal feature meets the predetermined feature condition may be obtained from the machine learning model. In some embodiments, the predetermined feature condition identification model may be a trained machine learning model. The training process of the predetermined feature condition identification model may be the same as or similar to the training process of the feature extraction model.

The processing device 120 may process the signal feature spectrum image of the sensing signal by using the trained predetermined feature condition identification model, and determine whether the signal feature in the signal feature spectrum meets the predetermined feature condition. In some embodiments, the predetermined feature condition identification model may include a neural network model, a logical regression model, a support vector machine, or the like. For example, taking the neural network model as an example, the neural network model may include a plurality of layers, such as an input layer, one or more convolutional layers, one or more nonlinear activation layers, one or more pooling layers, one or one fully connected layers, and/or an output layer. The neural network model may obtain the signal feature spectrum in the input layer, extract and/or distinguish visual features or patterns from an image by using an intermediate layer, and output the signal feature spectrum with features or patterns of feature points in the output layer. For example, the identified feature points may be marked with feature identifiers or feature vectors. In some embodiments, the identified feature points may be representative signal feature points, such as a highest point and a lowest point of a vibration peak, an end point and a start point of a vibration peak, etc.

In some embodiments, when the signal feature meets the predetermined feature condition, the processing device 120 may determine an operation of the target object corresponding to the predetermined feature condition.

In some cases, the user often inadvertently or inevitably performs certain actions to generate vibration signals, causing the target object to perform a false operation (e.g., switching the terminal device 130 from a first state to a second state). For example, taking the indoor environment 600 shown in FIG. 6 as an example, when a user sleeps on the bed 620, his hand or head may touch the headboard 630 by mistake, thereby generating a vibration signal. The vibration signal may be collected by a vibration sensing device arranged on the headboard 630 to generate a corresponding sensing signal. For example, if the signal feature of the sensing signal just meets the predetermined feature condition that the operation instruction is to turn on the light 640, the processing device 120 may control the light 640 to turn on by mistake, affecting the user's sleep, which may reduce user experience to a certain extent.

Therefore, in order to avoid the above situation, in some embodiments, the processing device 120 may screen the sensing signal obtained from the vibration sensing device. The processing device 120 may obtain a sensing signal of the at least one vibration sensing device in real-time or intermittently. When the processing device 120 obtains the sensing signal (also referred to as a first sensing signal), the processing device 120 may reserve a signal that an interval between the signal and the first sensing signal is within a range of a threshold time (e.g., 1 s, 2 s, 3 s, 5 s, 10 s, 15 s, etc.) as a sensing signal. In some embodiments, the processing device 120 may determine whether the first sensing signal is greater than a signal threshold. The signal threshold may be a parameter to measure whether the sensing signal is generated by a mistake touch of the user or a conscious action of the user. In some embodiments, the signal threshold may be a threshold of the signal strength. In some embodiments, the signal strength threshold may be 2 db~10 dB. In some embodiments, the signal strength threshold may be 4 dB~8 dB. In some embodiments, the signal strength threshold may be 6 dB. For example, when the first sensing signal is greater than the signal strength threshold, it may be considered that the first sensing signal is generated by a conscious action of the user. Therefore, the processing device 120 may designate a signal within a time range (e.g., a threshold time range) after the first sensing signal as the sensing signal. For a signal whose signal strength is less than the signal strength threshold, it may be considered that the first sensing signal is generated by a mistake touch of the user, therefore no processing may be performed.

In another application scenario, the user may have a pet cat, and the pet cat may scrap the door 610 to generate a vibration signal. The vibration signal may be collected by the vibration sensing device to generate a corresponding sensing signal. For example, if the signal feature of the sensing signal just meets the predetermined feature condition, and the operation instruction corresponding to the predetermined feature condition is to turn on or turn off the light 640, the light 640 may be turned on or turned off by mistake. Therefore, in some embodiments, the processing device 120 may prevent a false operation based on determining whether an object inputting the vibration signal is a user and a specific object designated by the user that may issue an operation instruction. In some embodiments, the processing device 120 may determine whether an object inputting the vibration signal is a user or a specific object that may issue an operation instruction based on information related to the object inputting the vibration signal. For example, a contour image of the object inputting the vibration signal may be obtained through a camera. It may be determined whether the object inputting the vibration signal is a user or a specific object that may issue an operation instruction according to the contour image. When the processing device 120 determines the object inputting the vibration signal is not a user or a specific object that may issue an operation instruction, the processing device 120 may not perform any operation.

Figure 6:
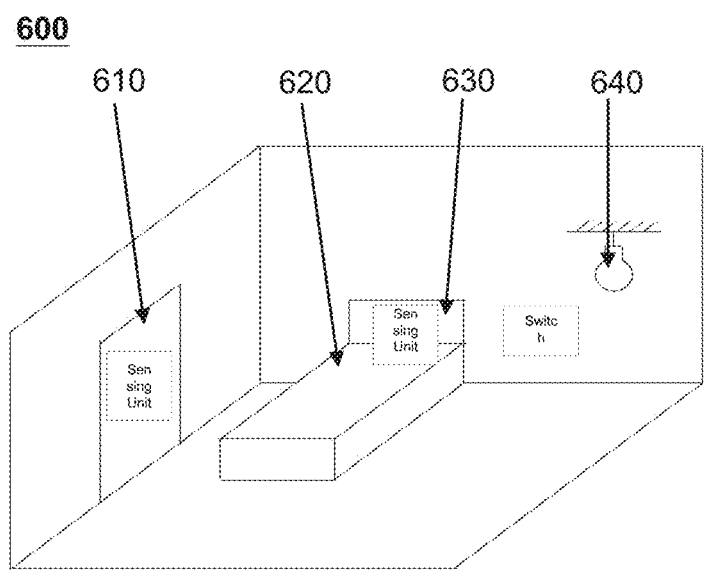
FIG. 6 is a schematic diagram illustrating an indoor environment provided with a terminal device according to some embodiments of the present disclosure.

FIG. 6 is a schematic diagram illustrating an indoor environment provided with a terminal device according to some embodiments of the present disclosure. Although the description of the technology described in the embodiment is described with reference to a home, a residence or a hotel, those skilled in the art may understand that features, processes, algorithms and mechanisms implemented through these technologies may be easily applied to other environments, such as an office, a warehouse, a garage or other environments.

In some embodiments, an indoor environment 600 may be a portion of the residence, a home environment, or a hotel. For example, the indoor environment 600 may be a bedroom or a living room of a residence of a user. For example, the indoor environment 600 may be one of rooms in a hotel where the user stays. In some embodiments, the indoor environment 600 may be provided with one or more terminal devices 130 (e.g., a light 640). One or more terminal devices 130 may be controlled by a processing device 120.

In some exemplary application scenarios, the door 610 may be installed at an entrance of the indoor environment 600. The light 640 (e.g., a light bulb, a fixture, a lamp, etc.) are installed on a side wall or top of the indoor environment 600. A switch of the light 640 may be provided on the side wall near the indoor light 640. The user may control the indoor light 640 to be turned off or turned on through the switch. A bed 620 may be installed at a connection between the floor and a side wall of the indoor environment 600. The bed 620 may include a headboard 630. In addition, the door 610 and the headboard 630 may be all physically connected (e.g., bonded) with a sensing device 110 (e.g., a vibration sensing device). The vibration sensing device may collect a vibration signal input by the user. The processing device 120 may identify a signal feature of the sensing signal and determine whether the signal feature meets a predetermined feature condition. When the processing device 120 determines that the signal feature meets the predetermined feature condition, an operation instruction may be sent to a target object (e.g., the switch of the light 640), and the target object may be controlled to perform an operation (e.g., turning on, turning off, color temperature adjustment, brightness adjustment, etc. of the light 640).

For example, when the user enters the indoor environment 600 at night (e.g., when the user comes home from work and enters the living room or the bedroom at night), the user may need to turn on the light 640. A vibration sensing device may be provided on the door 610. The user may input the vibration signal by knocking, patting, or scraping on the door 610. Based on a determination that the signal feature of the sensing signal generated by the vibration signal meets the predetermined feature condition, the light 640 may be controlled (e.g., turning on the light), which may be more convenient and safer compared with walking to the side wall to turn on the switch. In some embodiments, a specific area on the door 610 may serve as a vibration receiving area. For example, a door handle may serve as a vibration receiving area. When the user opens the door 610, the user may issue an operation instruction to turn on the light by knocking, patting, scraping in the vibration receiving area. As another example, a surface of the door 610 may serve as a vibration receiving area. The vibration sensing device may be connected to the vibration receiving area through the surface of the door 610 and receive the vibration signal input to the vibration receiving area. The vibration sensing device may be provided at a position, such as, a center of the door 610, an edge of the door 610, etc. In some embodiments, since the center of the door 610 has a high amplitude when the user knocks or pats, the vibration sensing device may be provided (e.g., inlaid or bonded) in the center of the door 610.

In some embodiments, a specific area of a surface of the door 610 facing away from the indoor environment 600 may serve as a vibration receiving area. For example, the vibration receiving area may be located on an upper side of the surface of the door 610 facing away from the indoor environment 600, so that the user may perform a specific operation with the hand to input a vibration signal. As another example, the vibration receiving area may be located on a lower side of the surface of the door 610 facing away from the indoor environment 600, so that the user may input the vibration signal by kicking the door 610 with a foot.

Figure 7:
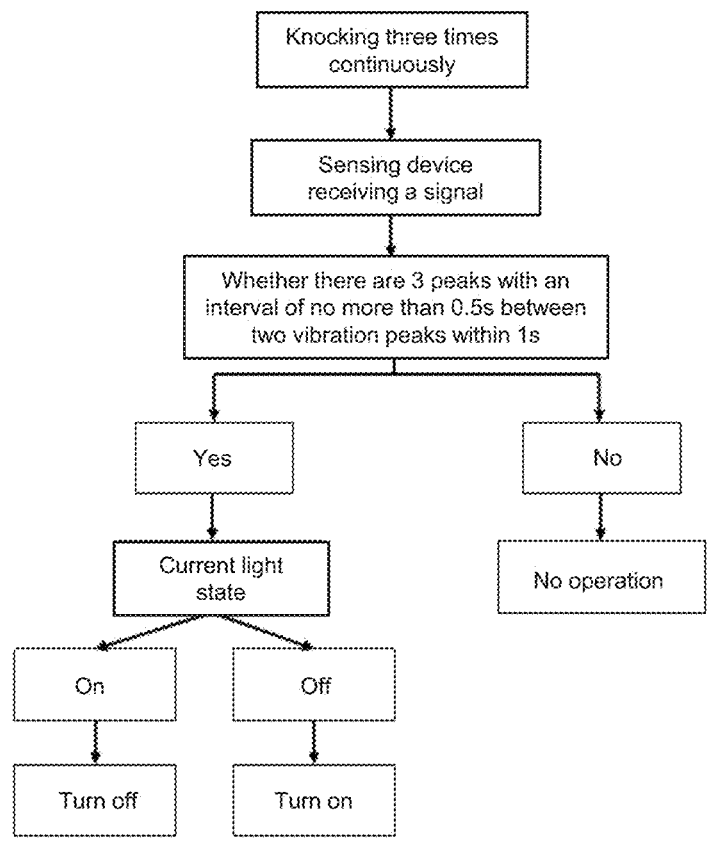
FIG. 7 is a flowchart illustrating an exemplary process for controlling a light in an indoor environment according to some embodiments of the present disclosure.

FIG. 7 is a flowchart illustrating an exemplary process for controlling a light in an indoor environment according to some embodiments of the present disclosure. In this embodiment, when the user knocks the headboard 630 three times continuously, the vibration sensing device provided on the headboard 630 or mechanically connected with the headboard 630 may receive the vibration signal and generate a corresponding sensing signal. The processing device 210 (e.g., a chip of a vibration sensing device) may perform feature identification on the sensing signal, and determine whether the sensing signal has three vibration peaks within 1 s with an interval of no more than 0.5 s between two vibration peaks. If so, a current light state of the light 640 may be continuously determined. If the light 640 is in an on state (that is, a first state), an instruction of turning off the light 640 may be issued to adjust the light 640 to an off state (that is, a second state). If the lamp 640 is in the off state (that is, the second state), an instruction of turning on the light 640 may be issued to adjust the light 640 to the on state (that is, the first state). If the processing device 210 determines that the sensing signal does not have three vibration peaks within 1 s, or the time interval between two adjacent vibration peaks exceeds 0.5 s, no operation may be performed.

If the switch is not on the bedside, the user may need to look for the switch in the dark when getting up at night, and there may be a risk of falling or bumping. If a vibration sensing device is installed on the headboard 630, the light 640 may be controlled by performing a specific operation on the headboard 630, which may be not only safer, but also more convenient.

In some embodiments, there may be a plurality of switches and buttons arranged around the bed 620. For example, when the indoor environment 600 is one of the rooms of a hotel, a plurality of switches for controlling the target object (e.g., the light 640) may be usually provided near the headboard 630 of the bed 620. When needing to control a specific target object, the user may need to look for a specific switch. If a vibration sensing device is installed on the headboard 630, the target object may be controlled by simple knocking, patting, scraping, or any combination thereof (e.g., turning off the light 640 with a specific operation).

In some embodiments, the arrangement of the indoor environment 600 may be not limited to may not be limited to FIG. 6. For example, the indoor environment 600 may also be provided with other target objects, such as a smart television, curtains, an air conditioner, etc. The user may control the other target objects through a system 100. For example, curtains may be provided on the side wall of the indoor environment 600, and the user may control the curtains by the system 100. For example, the headboard 630 may be knocked at a same time interval or a similar time interval within 1 s to control the curtains to be drawn or drawn back.

Figure 8:
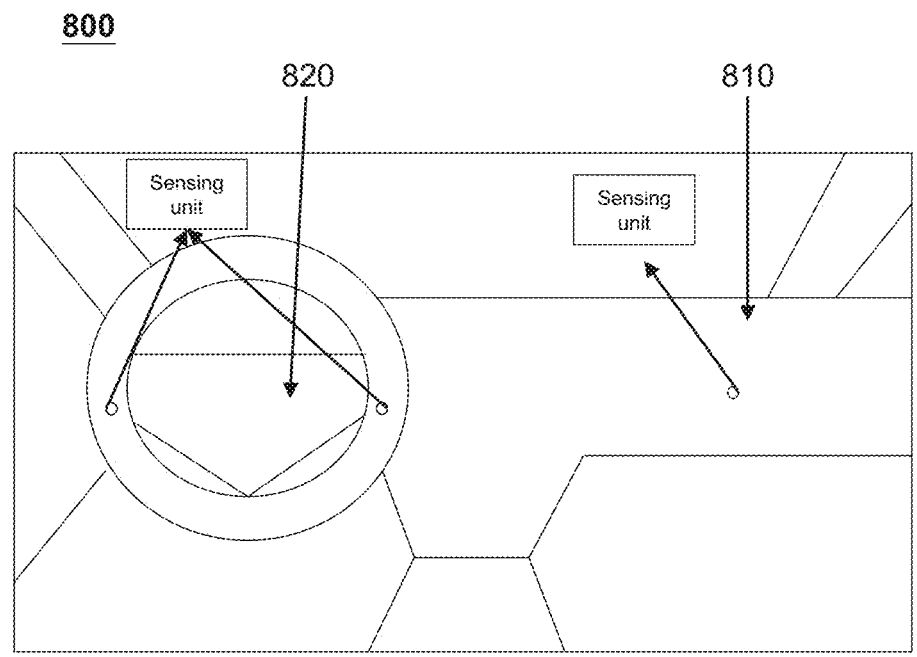
FIG. 8 is a schematic diagram illustrating an in-vehicle environment provided with a terminal device according to some embodiments of the present disclosure.

FIG. 8 is a schematic diagram illustrating an in-vehicle environment provided with a terminal device according to some embodiments of the present disclosure. In some embodiments, the in-vehicle environment 800 may include one or more terminal devices (such as a vehicle-mounted air conditioner, a vehicle-mounted speaker, car windows, etc.). The one or more terminal devices may be controlled by a system 100.

In some exemplary application scenarios, a sensing unit (e.g., a vibration sensing device) may be provided on a passenger seat storage box 810. The vibration sensing device may be associated with a vehicle-mounted air conditioner on a side of the passenger seat. The user may control the vehicle-mounted air conditioner on the side of the passenger seat via the system 100. For example, the user may continuously knock or pat a surface of the passenger seat storage box 810. The vibration sensing device may generate a sensing signal after receiving the vibration signal generated by the knocking or patting. The system 100 may identify the signal feature of the sensing signal and determine whether the signal feature meets a predetermined feature condition. For example, the predetermined feature condition may correspond to an operation of turning on/turning off the vehicle-mounted air conditioner. If the signal feature meets the predetermined feature condition, the system 100 may control the vehicle-mounted air conditioner on the side of the passenger seat to be switched on/off.

In some exemplary application scenarios, at least one sensing unit (e.g., a vibration sensing device) may be physically connected to a steering wheel 820. The vibration sensing device may be associated with a terminal device such as a vehicle-mounted air conditioner, a vehicle-mounted speaker, a car window, etc. Similarly, the user may control the vehicle-mounted air conditioner, the vehicle-mounted speaker, the car window, etc. through the system 100.

Figure 9:
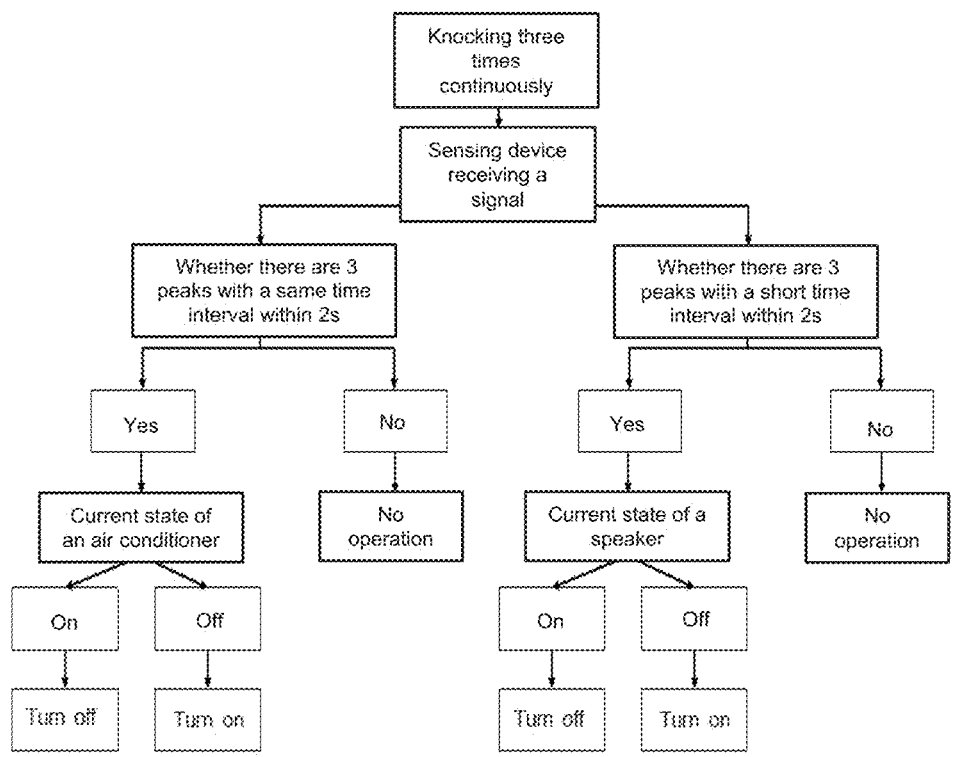
FIG. 9 is a flowchart illustrating an exemplary process for controlling an in-vehicle terminal device according to some embodiments of the present disclosure.

FIG. 9 is a flowchart illustrating an exemplary process for controlling an in-vehicle terminal device according to some embodiments of the present disclosure. In the embodiment, when a driver knocks a steering wheel 820 three times continuously, a vibration sensing device provided on the steering wheel 820 may collect a vibration signal and generate a sensing signal. A system 100 may identify a signal feature of the sensing signal and determine whether the signal feature meets a predetermined feature condition. As an example, the system 100 may identify whether the sensing signal has three vibration peaks at a same time interval or a similar time interval within 2 s (that is, a count of vibration peaks may be 3, and the time interval between two adjacent vibration peaks may be the same or similar). If not (that is, the signal feature of the sensing signal does not meet the predetermined feature condition), no operation may be performed. If so (that is, the signal feature of the signal meets the predetermined feature condition), a current state of the vehicle-mounted air conditioner may be obtained. If the vehicle-mounted air conditioner is in an on state (that is, a first state), an instruction to turn off the vehicle-mounted air conditioner may be issued to adjust the vehicle-mounted air conditioner to an off state (that is, a second state). If the vehicle-mounted air conditioner is in the off state, an instruction to turn on the vehicle-mounted air conditioner may be issued to adjust the vehicle-mounted air conditioner to an off state. As another example, the system 100 may identify whether the signal has three vibrational peaks with unequally time intervals within 2 s. (e.g., the time interval between a first vibration peak and a second vibration peak may be 1 s, and the time interval between the second vibration peak and a third vibration peak may be 2 s). If not (that is, the signal feature of the sensing signal does not meet the predetermined feature condition), no operation may be performed. If so (that is, the signal feature of the signal meets the predetermined feature condition), a current state of the vehicle-mounted speaker may be obtained. If the vehicle-mounted speaker is on, an instruction of turning off the vehicle-mounted speaker may be issued. If the vehicle-mounted speaker is off, an instruction of turning on the vehicle-mounted speaker may be issued.

In some embodiments, the arrangement of the in-vehicle environment 800 may be not limited to may not be limited to FIG. 8. For example, the in-vehicle environment 800 may also be provided with other target objects, such as a sunroof, a car seat heater, etc. In some specific embodiments, a roof of the in-vehicle environment 800 may be provided with a sunroof, and the user may control the sunroof through the system 100. For example, the steering wheel 820 may be knocked four times at a same time interval or a similar time interval within 1 s to control the sunroof to be closed or opened.

During the driving of the vehicle, the user (such as, a driver) may adjust the vehicle-mounted air conditioner and vehicle-mounted speaker. Manipulating the buttons, switches, etc. on the vehicle may distract driver's attention and may lead to a traffic safety accident. Although voice interaction may avoid the above problems to a certain extent, tire noise, music and a dialogue may cause great interference to voice interaction. Compared with the control method of voice interaction, by arranging the vibration sensing device at a specific position in the vehicle (e.g., the steering wheel 820), the driver may control target objects such as a vehicle-mounted air conditioner, a vehicle-mounted speaker, a sunroof, etc. by knocking, patting, or scraping in the vibration receiving area without taking his eyes away from the front of the vehicle, which may improve the safety of the vehicle driving.

Figure 10:
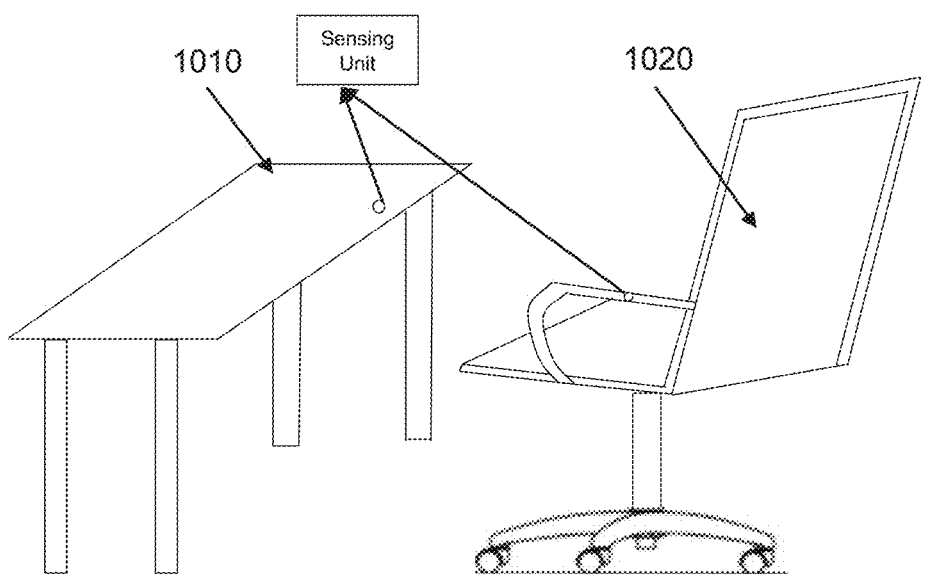
FIG. 10 is a schematic diagram illustrating a desktop environment provided with a terminal device according to some embodiments of the present disclosure.

FIG. 10 is a schematic diagram illustrating a desktop environment provided with a terminal device according to some embodiments of the present disclosure. The desktop environment 1000 may include one or more terminal devices. The terminal device may be one or more kinds of office and entertainment devices.

In some exemplary application scenarios, the desktop environment 1000 may include a table 1010 and a chair 1020. The table 1010 and/or the chair 1020 may be provided with sensing units (e.g., a first vibration sensing device provided on the table 1010 and a second vibration sensing device provided on the chair 1020). For example, the first vibration sensing device may be arranged on a surface of the table 1010, and the second vibration sensing device may be arranged on an armrest of the chair 1020. In some embodiments, the user may perform a specific operation in the vibration receiving area (e.g., any position on the surface of the table 1010 and/or the armrest of the chair 1020), and input a specific vibration signal to the vibration sensing device, so as to determine an operation or an operation instruction of the one or more office and entertainment devices. For example, if the vibration sensing signal corresponding to that the user knocks the desktop of the table 1010 with one finger meets a predetermined feature condition, the corresponding entertainment device (e.g., a musical instrument) may compose a song according to the rhythm of the user's finger knocking and play it through an external audio output device, which may make the user effectively relieve stress. As another example, the vibration sensing signal corresponding to that the user pats the armrest of the chair 1020 may meet the predetermined feature condition and an associated massage device may massage the user's back.

In some embodiments, the arrangement of the desktop environment 1000 may not be limited to that shown in FIG. 10. For example, the desktop environment 1000 may also include other terminal devices, such as a toy that may be pressed by the user. In some specific embodiments, the toy may include a vibration sensing device. When the user presses the toy, the vibration sensing device may collect a vibration signal and generate tactile feedback. For example, pressing the toy three times within 1 s may control the toy to continuously shake to massage the hand.

In some embodiments, a system 100 may also be applied to other usage scenarios. For example, a smart factory, a smart audio device. In some exemplary application scenarios, a smart factory may include an assembly line conveying device, a robotic arm, and a sensing unit (e.g., a vibration sensing device) installed in a common area. Under normal circumstances, the factory environment is relatively noisy or even full of high noise. Compared with voice interaction, the user may input vibration signals by performing specific operations such as knocking, patting, scraping, etc. in an area that is convenient to be operated to control devices such as an assembly line conveying device, a robotic arm or communicate with colleagues without being disturbed by noise, which may be convenient and easy for the user to control devices or communicate. For example, the user may knock at a same time interval at a similar time interval within 3 s. An operation instruction corresponding to the generated vibration signal may be to control the assembly line conveying device to start working. In some embodiments, the vibration sensing device may be arranged in an area far away from the robotic arm and the assembly line conveying device to prevent the vibration signal generated by the operating of the robotic arm and the assembly line conveying device from affecting the vibration signal input by the user.

In some exemplary application scenarios, the system 100 may be applied to a smart audio device (e.g., a smart speaker). For example, the smart speaker may include a vibration sensing device arranged (e.g., bonded) thereon. The smart speaker itself may communicate with the vibration sensing device (e.g., by means of a Bluetooth connection) as the terminal device. In some embodiments, the user may control the smart speaker by performing a specific operation, such as knocking, patting, scraping, etc. on the smart speaker. For example, the user may pat a housing of the smart speaker with a palm. The vibration sensing device may collect the vibration signal generated by the palm patting and generate a sensing signal. The system 100 may identify a signal feature, and then compare the signal feature with a predetermined feature condition. Based on the comparison result, an operation or an operation instruction corresponding to the sensing signal may be determined to play a next song. An interaction mode of the smart speaker may be mostly voice interaction, and a lack of tactile information may reduce the user's interaction experience. By arranging a vibration sensing device on the housing of the smart speaker, a tactile interaction between the user and the smart speaker may be established to enhance the interactive experience.

In some embodiments, the system 100 for controlling a target object may also monitor and analyze a body activity of the user (such as coughing, sneezing, snoring, yawning, falling, etc.), so as to accurately determine a physiological status of the user. For example, the system 100 may accurately and effectively collect a signal of the body activity of the user through a sensing device 110, and generate a corresponding sensing signal according to the signal. The system 100 may identify the signal feature of the sensing signal. Based on the signal feature, a physiological status of the user may be determined, and a health status of the user may be more accurately determined by the physiological status of the user. The sensing device 110 may be a vibration sensing device. In some embodiments, the sensing device 110 may also include a heart rate measurement part, a blood glucose measurement part, a blood pressure measurement part, a blood lipid measurement part, etc. In some embodiments, the system 100 may determine an operation or an operation instruction of the target object (e.g., a terminal device 130) based on the physiological status of the user. The operation instruction may be configured to control the target object to perform a corresponding function, so as to provide the user with more comprehensive health protection. An exemplary function may include recording a health status, issuing a warning, issuing an assistance request, or the like.

Figure 11:
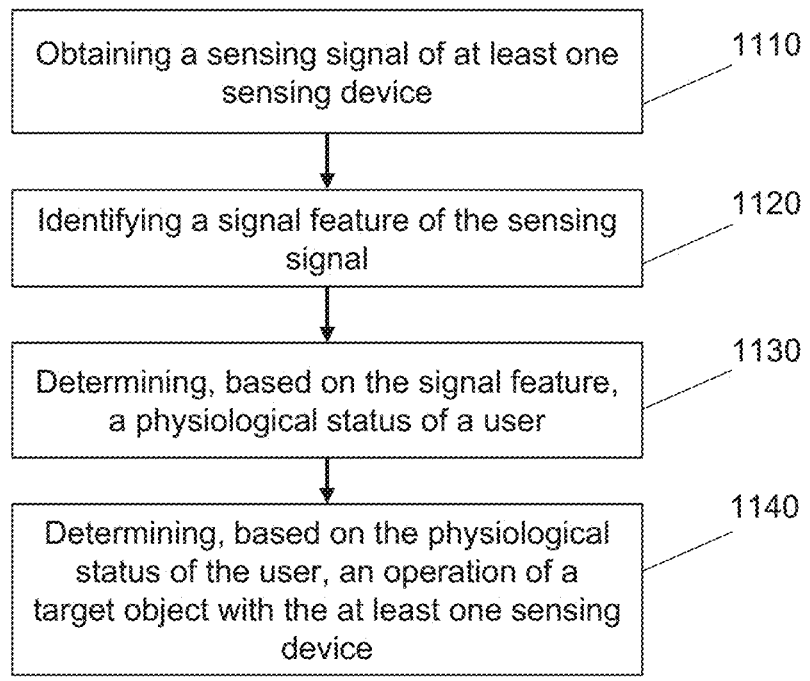
FIG. 11 is a flowchart illustrating an exemplary process for controlling a target object according to some embodiments of the present disclosure.

FIG. 11 is a flowchart illustrating an exemplary process for controlling a target object according to some embodiments of the present disclosure. Specifically, the method 1100 for controlling a target object may be performed by the system 100 for controlling a target object (e.g., a processing device 120). For example, the method 1100 for controlling a target object may be stored in a storage device (such as a self-contained storage unit of the processing device 120 or a storage device 140) in the form of a program or an instruction. When the method 1100 for controlling a target object may be implemented when the system 100 for controlling a target object (e.g., the processing device 120) executes the program or the instruction. The operation of the process below is merely for the purpose of illustration. In some embodiments, the process 1100 may be accomplished with one or more additional operations not described and/or without one or more of the operations discussed. In addition, an order of the operations of the process 1100 in FIG. 11 and described below is not restrictive. In some embodiments, the process 1100 may be applied in the field of human health monitoring.

In 1110, the processing device 120 may obtain a sensing signal of at least one sensing device. In some embodiments, the operation 1110 may be performed by a sensing signal obtaining module 310.

The at least one sensing device may include a vibration sensing device. The vibration sensing device may collect a vibration signal. For example, the vibration sensing device may be a microphone, an acceleration meter, etc. with bone conduction as one of main sound transmission manners. In some embodiments, the vibration sensing device may be arranged to a wearable device. An exemplary wearable device may include a smart bracelet, a smart footgear, a pair of smart glasses, a smart helmet, a smart watch, a smart clothing, a smart backpack, a smart accessory, or the like, or any combination thereof. When the user wears the wearable device, the wearable device may be attached to a body part of a user (e.g., a head, a neck, an ear, etc.). The vibration sensing device may receive the vibration signal generated by the body activity of the user through the wearable device. In some embodiments, the vibration sensing device may be an independent device. The vibration sensing device may be directly attached to a body part of the user and receive a vibration signal generated by a body activity of the user.

The vibration sensing device may be in direct or indirect contact with a body area of the user through the wearable device. The body activity of the user, such as coughing, sneezing, snoring, yawning, trembling, bumping, falling, etc. may generate a vibration signal. The vibration signal may be transmitted to the vibration sensing device via a bone or a muscle of the user. The vibration sensing device may obtain the vibration signal and generate a sensing signal. The vibration sensing device may be connected to the processing device 120. The processing device 120 may obtain the sensing signal generated by the vibration sensing device.

In 1120, the processing device 120 may identify a signal feature of the sensing signal. In some embodiments, the operation 1120 may be performed by a signal feature identification module 320. In some embodiments, the operation 1120 may be the same as or similar to the operation 420 in the process 400.

In some embodiments, the processing device 120 may process the vibration sensing signal (e.g., processing in time domain processing and/or processing in frequency domain, etc.), and output the vibration sensing signal as a signal feature spectrum. Based on the signal feature spectrum, the processing device 120 may identify the signal feature of the sensing signal. For example, the processing device 120 may read relevant information such as a count of vibration peaks, frequency components of a signal, etc. from the signal feature spectrum. In some embodiments, the processing device 120 may also directly identify the signal feature based on the relevant data/information of the vibration signal collected by the vibration sensing device. For example, the processing device 120 may calculate a time interval between two adjacent vibration peaks according to a time at which the two vibration peaks are obtained.

In some embodiments, the processing device 120 may identify at least one signal features of the sensing signal, such as a count of vibration peaks, a signal strength, a time interval between two adjacent vibration peaks, frequency components, a signal duration, or any combination thereof. Different body activities of the user, such as coughing, sneezing, snoring, yawning, trembling, bumping, falling, may generate different vibration signals (e.g., vibration signals with different frequency components, time intervals between two adjacent vibration peaks, durations and/or signal strengths). Correspondingly, the vibration sensing signal generated by the vibration sensing device may be also different (e.g., vibration sensing signals with different frequency components, time intervals between two adjacent vibration peaks, durations and/or signal strengths). For example, when the user sneezes, there may be many high-frequency signal components in the signal feature spectrum, and the duration of the vibration peak may be relatively long. When the user yawns, there may be many high-frequency signal components in the signal feature spectrum, and usually no obvious vibration peak may be generated. More description for the signal feature of the sensing signal corresponding to different body activities may be found elsewhere in the present disclosure, for example, FIGS. 12A-12E, which may not be described herein.

In 1130, the processing device 120 may determine, based on the signal feature, a physiological status of a user. In some embodiments, the operation 1130 may be performed by an operation determination module 330.

The physiological status herein may refer to a status in which the body of the user is located. Each body activity of the user may have a corresponding physiological status. The physiological status of the user may be a dangerous physiological status or a non-dangerous physiological status. The non-dangerous physiological status may include a coughing status, a sneezing status, a snoring status, a yawning status, etc. The dangerous physiological status may include a trembling status, a bumping status, a falling status, etc. The processing device 120 may determine the signal feature by analyzing and processing the sensing signal generated by the vibration sensing device, and then determine the physiological status of the user based on the signal feature.

In some embodiments, the processing device 120 may determine whether the identified signal feature meets at least one of a plurality of predetermined feature conditions. The predetermined feature condition may include one predetermined feature, a plurality of predetermined features, or any combination thereof. In some embodiments, the processing device 120 may use the signal feature corresponding to the physiological status as the predetermined feature condition. In some embodiments, each predetermined feature condition may correspond to a physiological status of the user. For example, the predetermined feature condition may be that two or more vibration peaks with small time intervals appear within a threshold time (e.g., 5 s, 8 s, 10 s, 15 s, etc.). As another example, the predetermined feature condition may be that there are many high-frequency signal components in the signal feature spectrum, and there is no obvious vibration peak. As another example, the predetermined feature condition may be that there are many low-frequency signal components in the signal feature spectrum. Each predetermined feature condition may correspond to different physiological statuses. For example, the predetermined feature condition may be that the physiological status corresponding to two or more vibration peaks with small time intervals within 10 s is a coughing status. As another example, the physiological status corresponding to the predetermined feature condition that the high-frequency signal components in the signal feature spectrum account for 60%, and there is no obvious vibration peak may be a yawning status. As another example, the physiological state corresponding to the predetermined feature condition that the low-frequency signal components in the signal feature spectrum account for 70% may be a falling status.

In some embodiments, the predetermined feature condition corresponding to each physiological status may be determined based on the signal feature of the sensing signal generated by actual body activities of a plurality of users.

For example, the predetermined feature condition corresponding to the yawning status may be determined by extracting the signal feature of the vibration sensing signal generated by the vibration sensing device when a plurality of users are yawning. In some embodiments, the processing device 120 may use the predetermined feature condition to determine a model, and determine the predetermined feature of each physiological status based on the extracted signal feature. The predetermined feature condition determination model may be, for example, a machine learning model. In some embodiments, the predetermined feature condition determination model may be a trained machine learning model. The training process of the predetermined feature condition determination model may be the same as or similar to the training process of the feature extraction model.

In some embodiments, the processing device 120 may determine whether the signal feature meets the predetermined feature condition based on the difference between the signal feature of the sensing signal and the predetermined feature condition. For example, the predetermined feature condition may include three or more vibration peaks appearing within 5 s. The processing device 120 may determine a count of vibration peaks that appear in the collected sensing signal within 5 s. If there are only two vibration peaks, the predetermined feature condition may be not met. In some embodiments, the processing device 120 may determine whether the signal feature meets the predetermined feature condition based on the signal feature spectrum of the sensing signal and the signal feature spectrum of the predetermined feature condition. For example, the processing device 120 may compare the signal feature spectrum of the sensing signal with the signal feature spectrum of the predetermined feature condition. If signal curves in the two signal feature spectra overlap or are similar, it may be determined that the signal feature meets the predetermined feature condition. In some embodiments, the processing device 120 may also determine whether the signal feature meets the predetermined feature condition based on a predetermined feature condition identification model. When the signal feature meets the predetermined feature condition, the processing device 120 may determine the physiological status corresponding to the predetermined feature condition as the physiological status of the user.

In 1140, the processing device 120 may determine, based on the physiological status of the user, an operation of a target object with the at least one sensing device 110. In some embodiments, the operation 1140 may be performed by an operation determination module 330. In some embodiments, the processing device 120 may further determine an operation instruction configured to control the target object to perform the operation. The operation instruction may instruct the target object (e.g., a smart wearable device, a terminal device 130, etc.) to perform an operation.

In some embodiments, the processing device 120 may determine the operation of the target object according to whether the physiological status is dangerous. In some embodiments, when the physiological status is a dangerous physiological status, for example, when the user is in a falling state, the processing device 120 may control operations of the terminal device 130 (e.g., a mobile terminal), such as, issuing an audio inquiry (e.g., "are you in danger?", "do you need any assistance?"), issuing a warning (e.g., issuing a warning to a pre-stored contact through a mobile terminal (such as a mobile phone), requesting external assistance (e.g., sending an assistance request to a public security organ and a hospital), or any combination thereof.

In some embodiments, when the physiological status is a non-dangerous physiological status, for example, when the user is yawning, the processing device 120 may record relevant information of the sensing signal. The relevant information of the sensing signal may include a frequency of the sensing signal (configured used to reflect a frequency of the body activity), a signal feature of the sensing signal (configured to reflect a type of the body activity), a time when the sensing signal appears (configured to reflect a specific time point or a time period of the body activity), or the like. In some embodiments, the processing device 120 may evaluate the health status of the user according to the recorded signal feature. For example, when the frequency of snoring exceeds a frequency threshold, the processing device 120 may determine that the user may have a disease in the throat. When the frequency of sniffing or sneezing of the user exceeds a frequency threshold, the processing device 120 may determine that the user may have a cold. In some embodiments, the processing device 120 may send and/or send the evaluation of the health status of the user to the terminal device 130 (e.g., a mobile phone) for the user to view.

In some embodiments, the processing device 120 may determine the operation of the target object in combination with the relevant information of the user. The relevant information of the user may include a medical history, an age, and various physiological parameters (e.g., a blood pressure, a blood glucose, a heart rate, etc.) of the user. In some embodiments, the relevant information of the user may be input by the user through the terminal device 130 (e.g., through a mobile terminal in communication with the processing device 120). In some embodiments, the at least one sensing device may also include a heart rate measurement part, a blood pressure measurement part, a blood glucose measurement part, or the like, or any combination thereof. The various physiological parameters of the user (e.g., a blood pressure, a blood glucose, a heart rate, etc.) may be obtained through the at least one sensing device. For example, when the processing device 120 determines that the physiological status of the user is a falling status, the age of the user may be obtained, for example, if the age of the user is 80 years old, the processing device 120 may directly control the terminal device 130 (e.g., a mobile terminal) to issue a warning. As another example, when the age of the user is 20 years old, the processing device 120 may control the terminal device 130 (e.g., a mobile terminal) to issue an audio inquiry. In some cases, compared with young people, middle-aged and elderly people may be more harmful to their health after falling, so it may be necessary to issue a warning to family members and friends in time to provide help to the user.

Figure 12A:
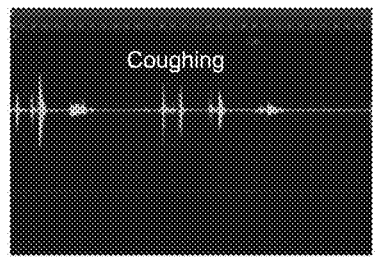
FIGS. 12A-12E are schematic diagrams illustrating signal feature spectra of vibration sensing signals corresponding to different body activities according to some embodiments of the present disclosure.
Figure 12B:
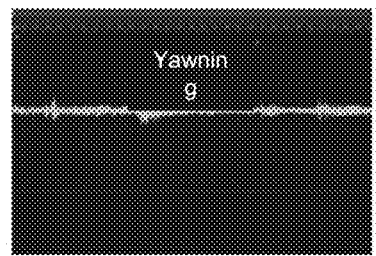
Figure 12C:
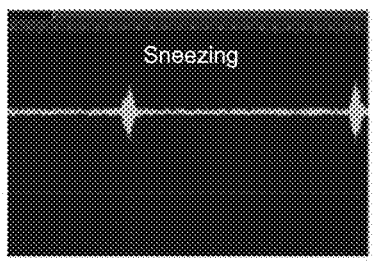
Figure 12D:
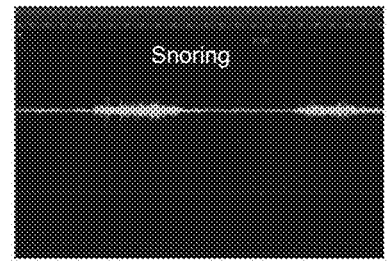
Figure 12E:
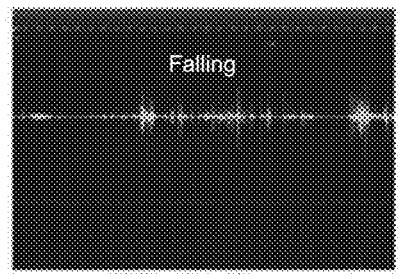

FIGS. 12A-12E are schematic diagrams illustrating signal feature spectra of vibration sensing signals corresponding to different body activities according to some embodiments of the present disclosure. FIG. 12A to FIG. 12E exemplarily show signal feature spectrum of vibration sensing signals generated by the user when coughing, yawning, sneezing, snoring, and falling, respectively. It may be seen from FIG. 12A to FIG. 12E that the vibration sensing signals caused by different body activities have different signal features. As shown in FIG. 12A, when the user coughs, it may generally continue to cough several times, so a plurality of vibration peaks with small intervals may appear. As shown in FIG. 12B, when the user yawns, there may be many high-frequency signal components in the signal feature spectrum, and usually no obvious vibration peak may be generated. As shown in FIG. 12C, when the user sneezes, there may be many high-frequency signal components in the signal feature spectrum, and the duration of the vibration peak may be relatively long. As shown in FIG. 12D, when the user makes a call, the high-frequency signal components in the signal feature spectrum may increase and concentrate. As shown in FIG. 12E, when the user falls, there may be more low-frequency signal components in the signal feature spectrum.

Figure 13:
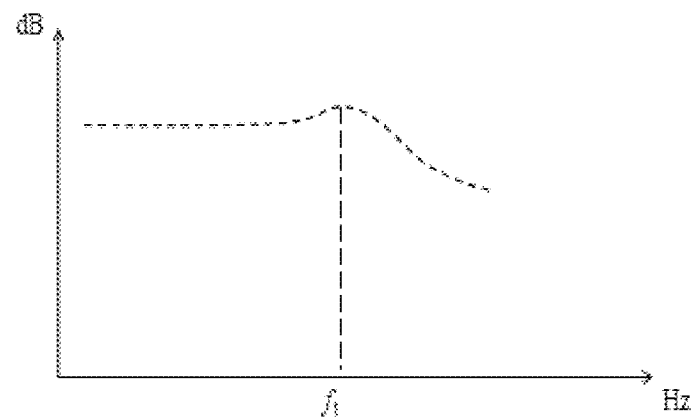
FIG. 13 is a schematic diagram illustrating a vibration sensing signal frequency curve of a body activity of a user according to some embodiments of the present disclosure.

FIG. 13 is a schematic diagram illustrating a vibration sensing signal frequency curve of a body activity of a user according to some embodiments of the present disclosure. As shown in FIG. 13, in some embodiments, a frequency of the vibration signal generated by the body activity of the user (e.g., coughing, sneezing, etc.) may be substantially lower than 5 kHz (a frequency at f1 may be 5 kHz). Therefore, a resonance frequency (that is, an inherent frequency) of the vibration sensing device may need to be less than 5 kHz. In some embodiments, the inherent frequency of the vibration sensing device may be 0.5 kHz~5 kHz. In some embodiments, the inherent frequency of the vibration sensing device may be 0.8 kHz~5 kHz. In some embodiments, the inherent frequency of the vibration sensing device may be 1 kHz~5 kHz. In some embodiments, the inherent frequency of the vibration sensing device may be 1.25 kHz~4.75 kHz. In some embodiments, the inherent frequency of the vibration sensing device may be 1.5 kHz~4.5 kHz. In some embodiments, the inherent frequency of the vibration sensing device may be 2 kHz~4.5 kHz. A sensitivity of the vibration sensing device may need to be as high as possible to make the obtained vibration signal more accurate. In some embodiments, the sensitivity of the vibration sensing device may be $(-50)$ dBV/$(m/s^2)$~$(-10)$ dBV/$(m/s^2)$. In some embodiments, the sensitivity of the vibration sensing device may be $(-35)$ dBV/$(m/s^2)$~$(-15)$ dBV/$(m/s^2)$. In some embodiments, the sensitivity of the vibration sensing device may be $(-30)$ dBV/$(m/s^2)$~$(-15)$ dBV/$(m/s^2)$. In some embodiments, the sensitivity of the vibration sensing device may be $(-25)$ dBV/$(m/s^2)$~$(-20)$ dBV/$(m/s^2)$.

Figure 14:
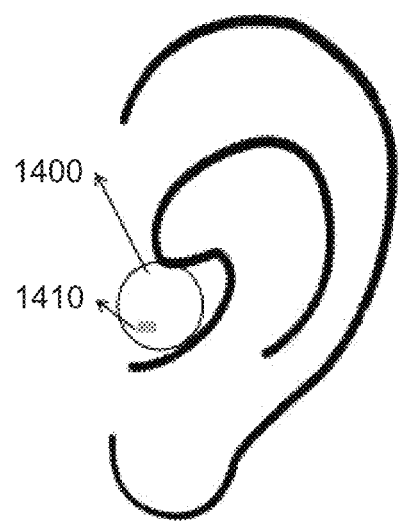
FIG. 14 is a schematic diagram illustrating that a system for controlling a target object is applied to a wearable device according to some embodiments of the present disclosure.

FIG. 14 is a schematic diagram illustrating that a system for controlling a target object is applied to a wearable device according to some embodiments of the present disclosure. For example, the wearable device may be a headset 1400. One or more components or units of the system 100 for controlling a target object may be integrated on the headset 1400.

In some embodiments, the headset 1400 may only have an audio output function, for example, the headset 1400 may be a speaker. In some embodiments, the headset 1400 may have an audio output and input function, such as a headset that may input and output audio. In some embodiments, the headset 1400 may be a hearing aid. In some embodiments, the headset 1400 may be a headset in which bone conduction or air conduction is one of the main transmission manners of sound. In some embodiments, the headset 1400 may be a headset (e.g., a monaural headset, a binaural headset), a supra-aural headset, an in-ear headset, etc.

In some embodiments, the headset 1400 may be the in-ear headset. A sensing device 1410 may be arranged on the headset 1400. The sensing device 1410 may be a vibration sensing device configured to collect a vibration signal generated by the body activity of the user. In some embodiments, the vibration sensing device may be a microphone in which bone sound conduction built in the headset is one of the main sound transmission manners. In some embodiments, the vibration sensing device may be a micro-electro-mechanical systems (MEMS) acceleration meter. The vibration sensing device 1410 may receive the vibration signal generated by the body activity of the user through the headset 1400. When the user wears 1400 headset, the headset 1400 may be attached to the body part of the user (e.g., an ear), and the vibration signal may be accurately transmitted to the vibration sensing device by the headset 1400. In some embodiments, by improving the connection stiffness between the vibration sensing device and the headset 1400, the loss of the vibration signal during transmission may be reduced, so that the vibration signal may be more accurately and completely collected by the vibration sensing device. In some embodiments, the vibration sensing device may be fixedly connected to a housing where the user contacts the headset 1400. Because the housing usually has a certain hardness, the loss of the vibration signal during transmission may be reduced. The means of fixed connection may include, but not limited to, inlaying, screw connection, riveting, welding, bonding, etc. In some embodiments, the vibration sensing device may be connected to the headset 1400 by means of bonding, so as to facilitate the disassembly of the vibration sensing device.

In some embodiments, the vibration sensing device may be directly attached to the body part (e.g., an ear) of the user. For example, when the user wears the headset 1400, the vibration sensing device may be arranged on a housing of the headset 1400 and directly contact the user's ear. The vibration signal generated by the user's body activity may be directly collected by the vibration sensing device without being transmitted through one or more parts of the headset 1400 (e.g., the housing), thereby reducing the loss of the vibration signal during transmission.

In some embodiments, in order to ensure that the wearable device (e.g., a smart headset, a pair of smart glasses, a smart helmet, etc.) have a reasonable overall size, there may be certain requirements for a volume of the vibration sensing device. In some embodiments, the volume of the vibration sensing device may be between 1 mm$^3$ and 10 cm$^3$. In some embodiments, the volume of the vibration sensing device may be between 0.5 mm$^3$ and 20 cm$^3$. In some embodiments, the volume of the vibration sensing device may be between 1.5 mm$^3$ and 5 cm$^3$. In some embodiments, the volume of the vibration sensing device may be between 2 mm$^3$~1 cm$^3$.

Figure 15:
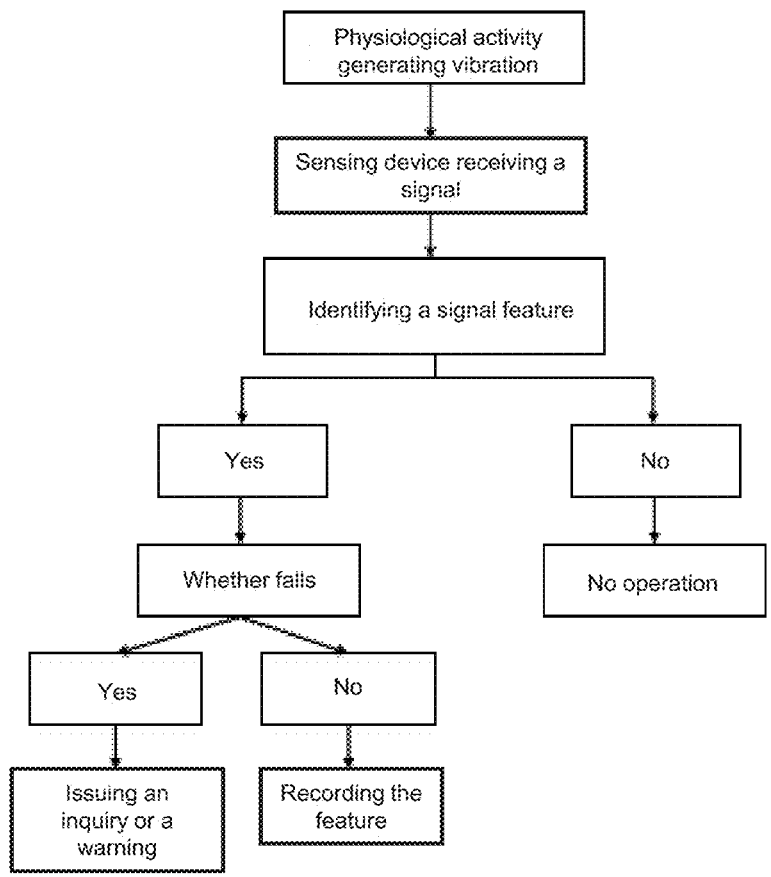
FIG. 15 is a flowchart illustrating an exemplary process for determining an operation of a target object based on a vibration signal generated by a body activity of a user according to some embodiments of the present disclosure.

FIG. 15 is a flowchart illustrating an exemplary process for determining an operation of a target object based on a vibration signal generated by a body activity of a user according to some embodiments of the present disclosure. In this embodiment, the vibration signal generated by the body activity of the user wearing a headset 1400 may be transmitted to the vibration sensing device fixedly connected to the headset 1400. The vibration sensing device may generate a corresponding vibration sensing signal after receiving the vibration signal. The processing device 120 may obtain the sensing signal generated by the vibration sensing device and identify the signal feature in the sensing signal. In some embodiments, the processing device 120 may determine whether the signal feature meets at least one of a plurality of predetermined feature conditions. For example, the predetermined feature condition may be a signal feature corresponding to a coughing status, a yawning status, a sneezing status, a sniffing status, a snoring status, a falling status, or the like, or any combination thereof. In some embodiments, if the signal feature of the sensing signal does not meet any one of the predetermined feature conditions, the processing device 120 may not perform an operation. In some embodiments, if the signal feature of the sensing signal meets one of the predetermined feature conditions, the processing device 120 may determine a physiological status corresponding to the predetermined feature condition. The processing device 120 may further determine whether the physiological status corresponding to the predetermined feature condition is a dangerous physiological status such as a falling status or a bumping status. In some embodiments, when the physiological status is the falling status, the processing device 120 may determine an operation of the target object corresponding to the dangerous physiological status. For example, a target object may include the headset 1400 and other devices that communicate with the headset 1400. For example, other devices that communicate with the headset 1400 may be a mobile terminal, such as a mobile phone. In some embodiments, the processing device 120 may issue an operation instruction to the headset 1400 so that the headset 1400 may issue an audio inquiry to the user: "are you in danger?", "do you need any assistance?" The user may reply to the audio inquiry to cause the processing device 120 to proceed. For example, the user may reply with an audio (e.g., the headset may have a voice input function) "rescue is needed", the processing device 120 may control the mobile terminal to issue a warning to a pre-stored contact, or request an external assistance. In some embodiments, if the processing device 120 does not detect the user reply within a certain time period (e.g., 10 s, 20 s, 30 s, etc.), the processing device 120 may issue a warning to a pre-stored contact, or request an external assistance. In some embodiments, when the physiological status is a non-dangerous physiological status (e.g., a coughing status, a yawning status, etc.), the processing device 120 may record relevant information of the sensing signal, so as to facilitate subsequent evaluation of the health status of the user.

Figure 16:
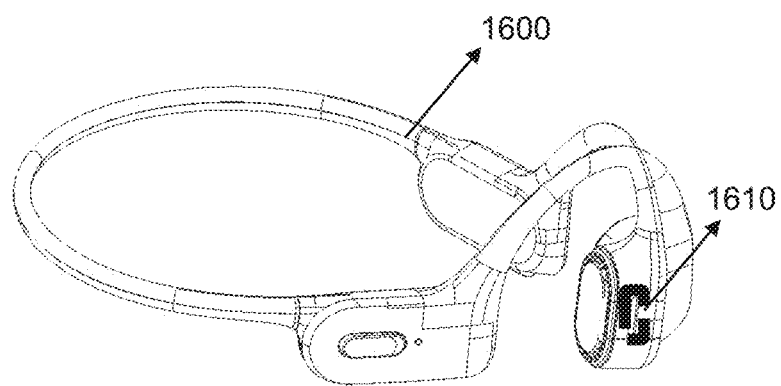
FIG. 16 is a schematic diagram illustrating that a system for controlling a target object is applied to a wearable device according to some embodiments of the present disclosure.

FIG. 16 is a schematic diagram illustrating that a system for controlling a target object is applied to a wearable device according to some embodiments of the present disclosure. For example, the wearable device may include a headset 1600 (e.g., a supra-aural headset). One or more components or units of the system 100 for controlling a target object may be integrated on the headset 1600 or communicatively connected with the headset 1600.

In some exemplary application scenarios, the sensing device 1610 may be arranged on the headset 1600. The sensing device 1610 may include a vibration sensing device configured to collect a vibration signal generated by the body activity of the user of the headset 1600 (e.g., shock when falling). An exemplary vibration sensing device 1610 may be a MEMS acceleration meter, a microphone in which bone conduction is one of the main sound transmission manners, etc. In some embodiments, the microphone in which bone conduction is one of the main sound transmission manners may be an element of the headset 1600. For example, the headset 1600 may be a headset including a microphone in which bone conduction is one of the main sound transmission manners. In some embodiments, the processing device 120 (e.g., a signal processing unit of the headset 1600) may determine the physiological status of the user based on the vibration sensing signal generated by the sensing device 1610. In some embodiments, the processing device 120 may determine the operation of the target object based on the physiological status of the user. The target object may refer to a terminal device 130 in the system 100. In some embodiments, the target object may include the headset 1600 and a smart terminal that communicates with the headset 1600. An exemplary smart terminal may include a mobile phone, a tablet computer, a bracelet, etc.

In other exemplary application scenarios, the sensing device 1610 may include a vibration sensing device and a motion sensing device. The motion sensing device may collect a motion signal related to a body posture of the user. An exemplary motion sensing device may include, but not limited to, a three-axis gyroscope, a three-axis acceleration meter, a three-axis electronic compass, etc. Taking the three-axis gyroscope as an example, the three-axis gyroscope may collect information/data related to a posture angle of the headset 1600 (e.g., an angular velocity of three orthogonal axes) and generate a corresponding sensing signal. The posture angle may include a pitch angle (i.e., an angle between the headset 1600 and the horizontal plane), a yaw angle and a roll angle. The processing device 120 may process the sensing signal to determine the signal feature thereof. Based on the signal feature, the processing device 120 may determine a body posture of the user. The body posture may include, for example, a stationary state, such as lying on the stomach, lying on the back, leaning the body at an angle, etc., or a motion state, such as standing up slowly, or the like. In some embodiments, a processor of the three-axis gyroscope (e.g., a chip) may also determine a body posture of the user based on the sensing signal. In some embodiments, the processing device 120 may determine a predetermined feature condition based on the corresponding signal features of a plurality of user body postures when in a stationary state (e.g., lying on the stomach, lying on the back, leaning the body at an angle) and in a motion state (e.g., standing up slowly). It may be determined whether the signal feature of the sensing signal meets the predetermined feature condition, so as to determine the body posture of the user. For example, when the signal feature of the sensing signal meets the predetermined feature condition corresponding to when the body posture is stationary (such as lying on the stomach), it may be determined that the body posture of the user is stationary (such as lying on the stomach).

In some embodiments, the processing device 120 may determine whether the user is in a falling state based on the signal feature of the sensing signal generated by the vibration sensing device. The processing device 120 may determine the body posture of the user based on the signal feature of the sensing signal generated by the motion sensing device. Combined with the sensing signal generated by the vibration sensing device and the motion sensing device, it may be determined whether the user falls and the body posture of the user. In some embodiments, the processing device 120 may determine a physiological status of the user based on a determination that whether the user is in a falling state and the body posture of the user. For example, the physiological status of the user may be divided into a dangerous status and a non-dangerous status. When the user is in a falling state and the body posture of the user is stationary (e.g., lying on the back) within a certain threshold time (e.g., 10 seconds, 20 seconds, 30 seconds, 1 minute, etc.), it may be determined that the user is in a dangerous status and needs help. As another example, when the user is not in a falling state or the user is in a falling state, but the body posture is in a motion state (e.g., standing up slowly), it may be determined that the user is in a non-dangerous status and does not need help.

In some embodiments, the processing device 120 may determine an operation of the target object based on the physiological status of the user. For example, when the processing device 120 determines that the user is in a falling state and the body posture of the user is stationary (e.g., lying on the side) within a threshold time, it may be determined that the user is in a dangerous status, and it may be determined that a mobile terminal (e.g., mobile phone) that is communicatively connected to the headset 1600 issues a warning or an external assistance request to a pre-stored contact. As another example, when the processing device 120 determines that the user is not in a falling state or the user is in a falling state, but the body posture of the user is in a motion state (such as standing up slowly, sitting up slowly, etc.), it may be determined that the user is in a dangerous status, and it may be determined that the mobile terminal communicatively connected to the headset 1600 records the relevant information of the sensing signal, so as to facilitate subsequent evaluation of the health status of the user.

In some embodiments, the headset 1600 may further include a physiological parameter sensing device. An exemplary physiological parameter sensing device may include a heart rate measurement part, a blood pressure measurement part, a blood glucose measurement part, etc. The physiological parameter sensing device may be configured to sense or analyze vasodilation, thoracic activity, blood composition, etc. of the user, and generate a sensing signal. The processing device 120 may identify the signal feature of the sensing signal and determine at least one physiological parameter of the user. An exemplary physiological parameter may include a heart rate, a blood pressure, a blood glucose, etc. For example, the physiological parameter sensing device may include a photoelectric sensing unit that obtains a pulse signal of the body part of the user (e.g., a wrist, an upper arm, a head, etc.), and determines the blood pressure of the user according to the pulse signal through the processing device 120. In some embodiments, a processor of the physiological parameter sensing device (e.g., a chip) may also determine the physiological parameter of the user based on the sensing signal.

Combined with the sensing signal generated by the vibration sensing device, the motion sensing device and/or the physiological parameter sensing device, the processing device 120 may determine whether the user falls, the body posture of the user and/or the at least one physiological parameter. In some embodiments, the processing device 120 may determine a physiological status of the user based on a determination that whether the user falls, the body posture of the user, and/or the physiological parameter. For example, the physiological status of the user may be divided into a dangerous physiological status and a non-dangerous physiological status. When the user is in a falling state and the body posture of the user is stationary (e.g., lying on the back) within a certain threshold time (e.g., 10 seconds, 20 seconds, 30 seconds, 1 minute, etc.), and the physiological parameter exceeds the threshold (e.g., the heart rate is lower than a predetermined heart rate threshold, the blood glucose is lower than a predetermined blood pressure threshold, the blood pressure is higher than a predetermined blood pressure threshold, etc.), it may be determined that the user is in a dangerous physiological status and needs help. The heart rate lower than a predetermined heart rate threshold, the blood glucose is lower than a predetermined blood glucose threshold, and/or the blood pressure is higher than a predetermined blood pressure threshold may be determined with reference to a heart rate, a blood glucose and/or a blood pressure of a normal human body. For example, the predetermined heart rate threshold may be 100 beats/min, 120 beats/min, 140 beats/min, 160 beats/min, or the like. As another example, when the user is not in a falling state or the user is in a falling state, but the body posture of the user is in a motion state (e.g., standing up slowly) or each physiological parameter is within a threshold range, it may be determined that the user is in a non-dangerous physiological status and does not need help.

Compared with determining merely based on the single condition that whether the user falls, it may be more accurate and effective to determine the physiological status of the user in combination with the body posture and/or the physiological parameter of the user, and the operation of the target object finally determined may be also more in line with the actual situation.

Figure 17:
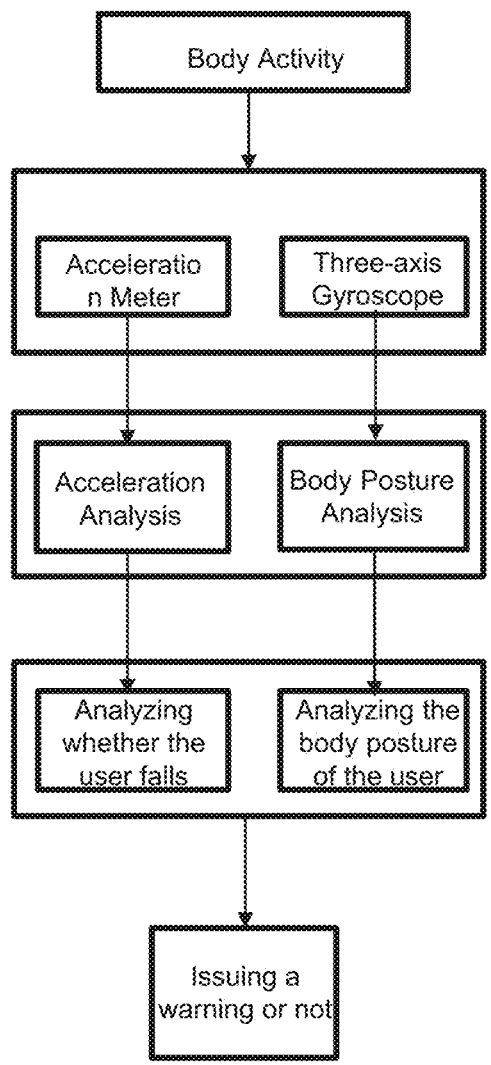
FIG. 17 is a flowchart illustrating an exemplary process for determining an operation of a target object based on a vibration signal generated by a body activity of a user.

FIG. 17 is a flowchart illustrating an exemplary process for determining an operation of a target object based on a vibration signal generated by a body activity of a user. This embodiment shows a process for determining an operation of a target object based on a vibration sensing device and a motion sensing device arranged on the wearable device (e.g., a headset 1600). For example, the vibration sensing device may be a MEMS acceleration meter (referred to as an acceleration meter). The motion sensing device may be a three-axis gyroscope. In this embodiment, the body activity of the user who wears the headset 1600 (e.g., bumping, falling, etc.), the generated vibration signal may be transmitted to the MEMS acceleration meter fixedly connected with the headset 1600. After the MEMS acceleration meter collects the vibration signal, a corresponding sensing signal may be generated. At the same time, the three-axis gyroscope may also collect information/data related to the posture angle of the user's body. In some embodiments, the processing device 120 (e.g., a signal processing unit of the headset 1600) may process the sensing signal generated after the MEMS acceleration meter collects the vibration signal, and identify the signal feature in the sensing signal, so as to determine whether the user falls. For example, the processing device 120 may perform acceleration analysis based on the sensing signal, so as to determine whether the user falls. The processing device 120 may process the sensing signal generated after the three-axis gyroscope collects the signal, and identify the signal feature in the sensing signal, so as to determine the body posture of the user. For example, the processing device 120 may perform body posture analysis based on the sensing signal, so as to determine the body posture of the user.

In some embodiments, the processing device 120 may determine whether to issue a warning in combination with a determination that whether the user falls and the body posture of the user. As mentioned above, when the processing device 120 determines that the user is in a falling state and the body posture of the user is stationary within a threshold time, it may be determined that the user is in a dangerous status, and it may be determined that the mobile terminal (e.g., a mobile phone) issues a warning to a pre-stored contact or requests an external assistance.

Figure 18:
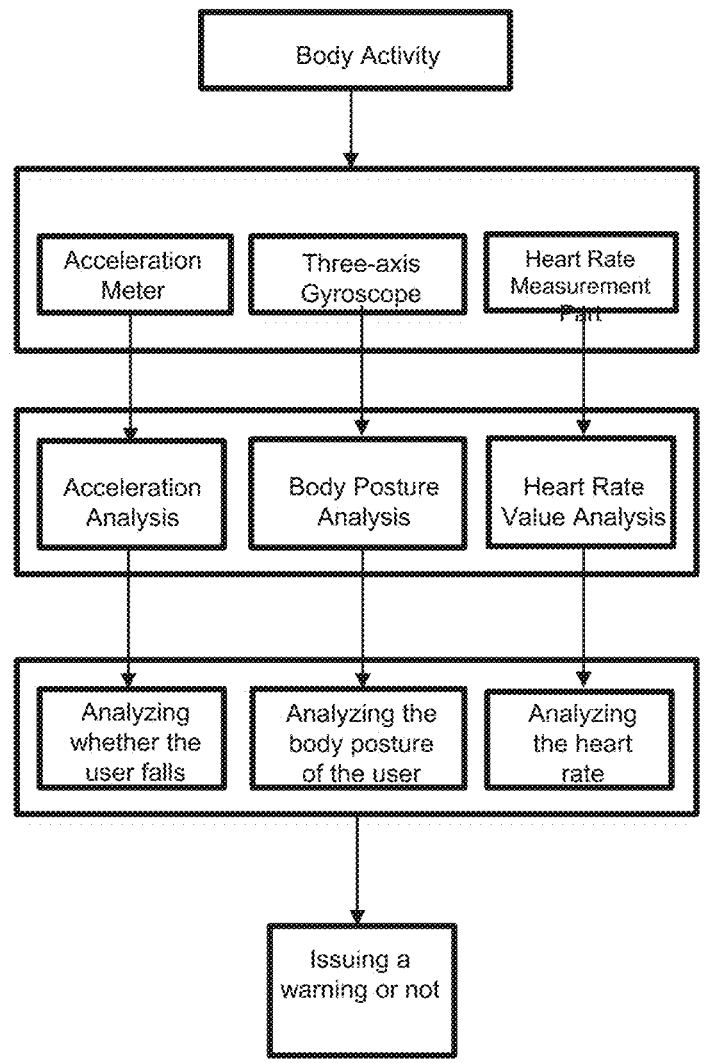
FIG. 18 is a flowchart illustrating an exemplary process for determining an operation of a target object based on a vibration signal generated by a body activity of a user.

FIG. 18 is a flowchart illustrating an exemplary process for determining an operation of a target object based on a vibration signal generated by a body activity of a user. This embodiment shows a process for determining an operation of a target object based on a vibration sensing device, a motion sensing device and a physiological parameter sensing device arranged on the wearable device (e.g., a headset 1600). For example, the vibration sensing device may be an acceleration meter. The motion sensing device may be a three-axis gyroscope. The physiological parameter sensing device may be a heart rate measurement part. In this embodiment, the body activity of the user who wears the headset 1600 (e.g., bumping, falling, etc.), the generated vibration signal may be transmitted to the MEMS acceleration meter fixedly connected with the headset 1600. After the MEMS acceleration meter collects the vibration signal, a corresponding sensing signal may be generated. The three-axis gyroscope may collect information/data related to the posture angle of the user's body. At the same time, the heart rate measurement part may also collect information/data related to the heart rate of the user. In some embodiments, the processing device 120 (e.g., a signal processing unit of the headset 1600) may process the sensing signal generated after the MEMS acceleration meter collects the vibration signal, and identify the signal feature in the sensing signal, so as to determine whether the user falls. For example, the processing device 120 may perform acceleration analysis based on the sensing signal, so as to determine whether the user falls. The processing device 120 may process the sensing signal generated after the three-axis gyroscope collects the signal, and identify the signal feature in the sensing signal, so as to determine the body posture of the user. For example, the processing device 120 may perform body posture analysis based on the sensing signal, so as to determine the body posture of the user. The processing device 120 may process the sensing signal generated after the heart rate measurement part collects the signal, and identify the signal feature in the sensing signal, so as to determine the heart rate of the user. For example, the processing unit 120 (e.g., a processing unit (e.g., a chip) of the heart rate measurement part) may perform heart rate value analysis based on the sensing signal, so as to determine the heart rate of the user.

In some embodiments, the processing device 120 may determine whether to issue a warning based on a determination that whether the user falls, the body posture of the user, and the heart rate of the user. For example, when the processing device 120 determines that the user is in a falling state, and the body posture of the user is stationary within a threshold time and/or the physiological parameter of the user exceeds a predetermined threshold (e.g., a diastolic pressure exceeds a predetermined diastolic pressure threshold (such as 140 mmHg, 160 mmHg, 160 mmHg, 180 mmHg, etc.), it may be determined that the user is in a dangerous status, and It may be determined that the mobile terminal issues a warning to a pre-stored contact or requests an external assistance.

In some cases, compared with determining the user's status merely through the body activity, it may be more accurate to confirm the user's status in combination with information of a determination that whether the user falls, the body posture of the user, the physiological parameter of the user, etc., and the operation of the target object final determined may be more in line with the actual situation, which may effectively monitor the body health status of the user.

Figure 19:
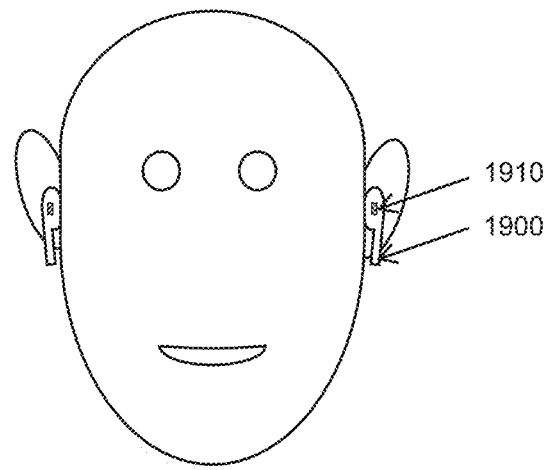
FIG. 19 is a schematic diagram illustrating that a system for controlling a target object is applied to a wearable device according to some embodiments of the present disclosure.

FIG. 19 is a schematic diagram illustrating that a system for controlling a target object is applied to a wearable device according to some embodiments of the present disclosure. A sensing device 110 in a system 100 for controlling a target object may include a vibration sensing device. The vibration sensing device may be integrated or arranged (e.g., bonding, buckle connection, etc.) in the wearable device. The vibration sensing device may be arranged at a specific position. The specific position may be a position that may relatively completely and clearly receive the vibration signal generated by the body activity of the user and transmitted through bones or muscles of the user. An exemplary specific position may include a nose bridge, an ear, a mouth, a throat, etc. of the user. In some embodiments, the position of the vibration sensing device may be related to a type of the wearable device. For example, when the wearable device is glasses, the vibration sensing device may be arranged on a nose bridge frame of the glasses or at a position where a temple is in contact with an ear. As another example, when the wearable device is a headset, the vibration sensing device may be arranged on the ear of the user. In some embodiments, the at least one vibration sensing device may include a single vibration sensing device arranged at a certain position or a plurality of vibration sensing devices arranged at different positions.

For example, the wearable device may include a headset 1900 (e.g., an in-ear headset). One or more components or units of the system 100 for controlling a target object may be integrated on the headset 1900 or communicatively connected with the headset 1900. For example, a vibration sensing device 1910 may be arranged on the headset 1900. The vibration sensing device 1910 may be integrated or arranged (e.g., bonding, buckle connection, etc.) in the headset 1900 to collect the vibration signal generated by the body activity of the user. In some embodiments, the vibration sensing device may be a microphone in which the bone conduction built in the headset is one of the main sound transmission manners. In some embodiments, the vibration sensing device may be a MEMS acceleration meter. As another example, the processing device 120 (e.g., a mobile phone or a computer) may be communicatively connected to the headset 1900 and the sensing device 110. The sensing device 1910 may be a vibration sensing device.

The vibration sensing device 1910 may receive the vibration signal generated by the body activity of the user through the headset 1900. When the user wears 1900, the headset 1900 may be attached to the body part of the user (e.g., an ear), and the vibration signal may be accurately transmitted to the vibration sensing device through the headset 1900. In some embodiments, the vibration sensing device may also be directly attached to the body part of the user (e.g., an ear). The vibration signal generated by the body activity of the user may be directly collected by the vibration sensing device without passing through the headset 1900. In this embodiment, the body activity of the user may refer to a tooth tapping and rubbing of the user. The user may generate a vibration signal by tapping or rubbing the tooth. The vibration signal may be transmitted to the vibration sensing device via bones or facial muscles of the user.

In some embodiments, the headset 1900 may be worn on one-sided ear of the user. For example, the headset 1900 may be a Bluetooth headset with a single speaker worn on the left or right ear of the user. At this time, the vibration sensing device 1910 may collect the vibration signal transmitted to the left or right ear of the user. In some embodiments, the headset 1900 may also be worn on both ears of the user. For example, the headset 1900 may be a headset, a supra-aural headset, an in-ear headset, etc. with two speakers. The two speakers may be respectively worn on the left and right ears of the user. At this time, the vibration sensing device 1910 may include two vibration sensing devices collecting vibration signals transmitted to the left and right ears of the user.

In some embodiments, the processing device 210 may receive the vibration sensing signal generated by the vibration sensing device 1910 and identify the signal feature of the vibration sensing signal. The processing device 210 may determine the operation of the target object based on the signal feature, for example, switching the target object from a first state to a second state. The target object may be the headset 1900 or a terminal device 130 (e.g., a mobile device (such as a smart wearable device), a tablet computer, a laptop computer, a built-in device in a vehicle (such as a vehicle engine system, an air conditioner, a car light, a windshield wiper, etc.), a smart home device (such as a light, a television, curtains, etc.), or the like, or any combination thereof). Detailed description for the operation of the processing device 210 determining the target object based on the vibration sensing signal may be found in FIG. 21 and the relevant descriptions in the present disclosure.

Compared with the way of controlling the terminal device (e.g., a wearable device) through a button, an operation panel, etc., issuing an operation instruction to the wearable device and other terminal devices by a tooth tapping frees up hands of the user, making it safer in certain situations (e.g., driving, cycling, and dark environment). At the same time, compared with the way of controlling the terminal device by sending a audio signal, issuing an operation instruction to the terminal device by a tooth tapping may be more secretive, which may not cause interference to the surrounding people, and may be also conducive to the confidentiality of the personal information of the user.

Figure 20:
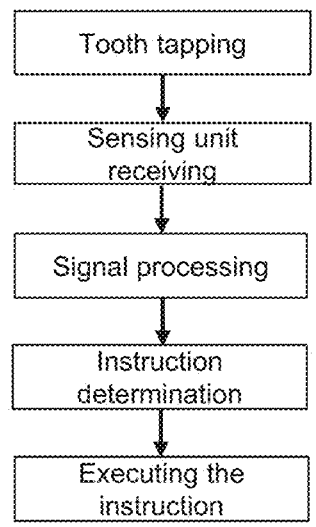
FIG. 20 is a flowchart illustrating an exemplary process for controlling a target object according to some embodiments of the present disclosure.
Figure 21:
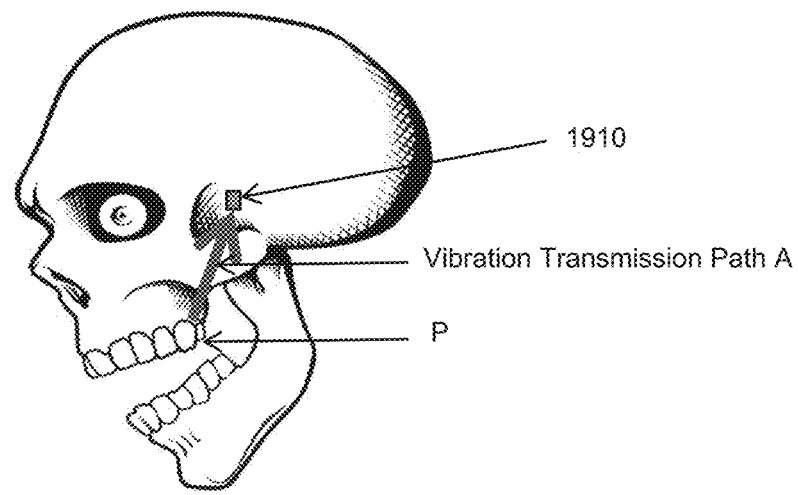
FIG. 21 is a schematic diagram illustrating vibration signal transmission according to some embodiments of the present disclosure.

FIG. 20 is a flowchart illustrating an exemplary process for controlling a target object according to some embodiments of the present disclosure. The vibration signal generated by the body activity of the user (e.g., a tooth tapping) may be transmitted to a vibration sensing device 1910 via the facial bones or muscles of the user. The process of vibration signal transmission may refer to FIG. 21. As shown in FIG. 21, the tooth tapping of the user may generate a vibration signal at the tapping point P, and the vibration signal may be transmitted to the vibration sensing device 1910 via the facial bone of the user. The path of the vibration signal transmitted from the point P to the vibration sensing device 1910 is shown as the transmission path A in the figure.

When the vibration sensing device 1910 collects the vibration signal, a corresponding vibration sensing signal may be generated. After receiving the vibration sensing signal, the processing device 120 may process the vibration sensing signal to identify the signal feature in the vibration sensing signal. The signal feature may include a count of vibration peaks, a time interval between two adjacent vibration peaks, a signal strength, frequency components, or a signal duration of the vibration sensing signal generated by the vibration sensing device. The count of vibration peaks of the vibration sensing signal may reflect a count of tooth tapping. The time interval between two adjacent vibration peaks of the vibration sensing signal may reflect a speed of tapping. The signal strength of the vibration sensing signal may reflect a strength of the tooth tapping. The frequency components of the vibration sensing signal may reflect whether there are other objects between the teeth (e.g., food). If other objects exist, the low-frequency components may increase. The signal duration of the vibration sensing signal may reflect a duration of an entire vibration sensing signal or a duration of a single vibration peak.

In some embodiments, the processing device 120 may determine whether the signal feature of the sensing signal meets one of a plurality of predetermined feature conditions. Each predetermined feature condition may correspond to at least one operation of the target object or an instruction for controlling the target object to perform the operation. In some embodiments, the processing device 120 may use the signal feature corresponding to a combination of specific tapping actions as a predetermined feature condition. For example, the signal feature corresponding to two consecutive tapping (a vibration peak time interval $\Delta t$ less than a first tapping interval threshold t0) may be designated as the predetermined feature condition. The predetermined feature condition may correspond to an operation of switch on/off of the headset 1900. For example, the signal feature corresponding to two slow tapping (a vibration peak time interval $\Delta t$ less than a first tapping interval threshold t0 and less than a second tapping interval threshold t1) may be designated as the predetermined feature condition. The predetermined feature condition may correspond to a play/pause operation of the headset 1900.

When the signal feature of the sensing signal meets one of the predetermined feature conditions, the processing device 120 may determine the operation of the target object corresponding to the sensing signal. For example, when the signal feature meets the predetermined feature condition of two consecutive tapping, the processing device 120 may control the headset 1900 to perform the operation of switch on/off. The processing device 120 may detect the state of the headset 1900. When the headset 1900 is in the on state (that is, a first state), it may be determined that the headset 1900 is adjusted to the off state (that is, a second state). When the headset 1900 is in the off state, it may be determined that the headset 1900 is adjusted to the on state.

Figure 24:
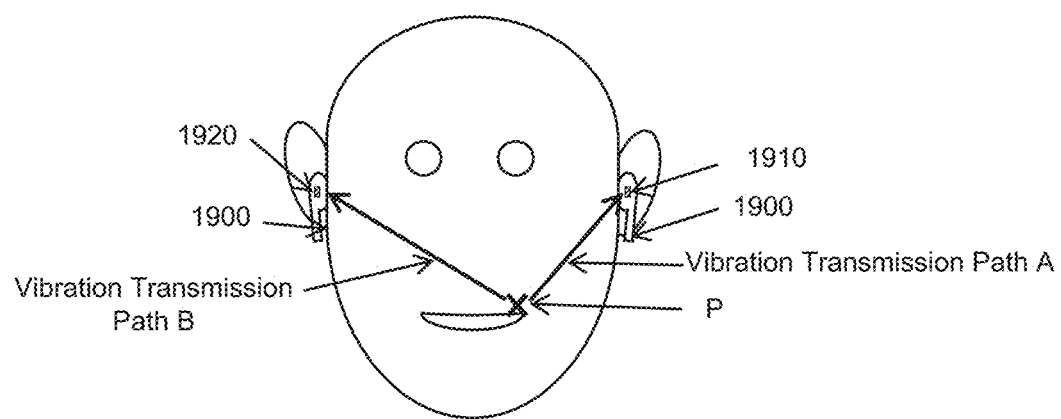
FIG. 24 is a schematic diagram illustrating that a system for controlling a target object is applied to a wearable device according to some embodiments of the present disclosure.

In some embodiments, when the vibration sensing device includes only the vibration sensing device arranged at a specific position (e.g., in FIG. 22, the vibration sensing device is only arranged at a right part of the headset 1900), the signal feature may include a count of vibration peaks, a time interval between two adjacent vibration peaks, and/or a signal duration vibration of the vibration sensing signal generated by the vibration sensing device. In some embodiments, when the sensing unit includes vibration sensing devices arranged at different positions (e.g., in FIG. 24, vibration sensing devices 1920 and 1910 are respectively arranged at left and right parts of the headset 1900), the signal feature of the sensing signal may also include a phase difference of sensing signals of vibration sensing devices at the different positions. The phase difference may be configured to determine a position of a vibration source (that is, the tapping point P of the tooth tapping). For example, as shown in FIG. 24, when the tapping point P is on the right side, distances between the tapping point P and the vibration sensing devices arranged at different positions may be different, therefore, lengths of the vibration transmission paths (e.g., the vibration transmission path B from the tapping point P to the vibration sensing device 1920 on the left and the vibration transmission path A from the tapping point P to the vibration sensing device 1910 on the right) may be different. The vibration sensing device 1910 on the right may first capture the vibration signal, and the vibration sensing device 1920 on the left may capture the vibration signal later. The vibration signals collected by the two vibration sensing devices 1910 and 1920 may have a phase difference. Based on the phase difference, the difference between the vibration transmission path B and the vibration transmission path A may be determined. Because the positions of the vibration sensing devices 1910 and 1920 are fixed, the position of the tapping point P (e.g., left, right, middle, etc.) may be determined.

In some cases, by positioning the vibration source (that is, the tooth tapping point P), the user may combine more types and more complex tooth tapping operations by changing the position of the tapping point P, the count of tapping and/or the tapping interval, etc., so as to correspond to more and more complex target object operations or operation instructions.

In some cases, the user may make a tooth tapping inadvertently or inevitably. For example, when the user is eating, a tooth tapping may occur. As another example, when the user is speaking, a tooth tapping may occur. For example, when the user experiences a body activity such as trembling, sneezing, etc. and an external shock (e.g., bumping), a tooth tapping may also occur. The above situation may trigger an operation of the target object (that is, a false trigger). In some embodiments, the processing device 120 may screen or identify the sensing signal to avoid the false trigger.

The processing device 120 may obtain the vibration sensing signal of at least one vibration sensing device in real-time or intermittently. When the vibration sensing signal (also referred to as a second sensing signal) is obtained, the processing device 120 may obtain the relevant information of the second sensing signal, such as a frequency, a signal strength, etc. The processing device 120 may determine whether the second sensing signal is a false trigger signal based on the relevant information of the second sensing signal. For example, the processing device 120 may determine whether the second sensing signal is a false trigger signal based on a frequency of the second sensing signal. For example, when the frequency of the second sensing signal is lower than a predetermined frequency threshold, the second sensing signal may be designated as a false trigger signal. When the frequency of the second sensing signal is lower than the predetermined frequency threshold, it may be considered that the user is eating. The sensing signal generated at this time may be designated as a false trigger signal, and the target object may not need to perform any operation.

In some embodiments, the sensing device 110 may also include an audio input device (e.g., a microphone). In some embodiments, the microphone may also be an element of a wearable device (e.g., the headset 1900). When the vibration sensing signal (also referred to as a third sensing signal) is obtained, the processing device 120 may determine whether the audio input device receives user audio information simultaneously. If the audio input device receives the user audio information, the third sensing signal may be designated as a false trigger signal. At this time, it may be considered that the user is talking with others or using a communication device to make a call. The sensing signal generated at this time may be designated as a false trigger signal, and the target object may not need to perform any operation.

In some embodiments, when the vibration sensing signal (also referred to as a fourth sensing signal) is obtained, the processing device 120 may determine whether the fourth sensing signal is the false trigger signal based on a false trigger identification model. In some embodiments, the false trigger identification model may be a machine learning model. In some embodiments, the processing device 120 may use the fourth sensing signal as input data of the machine learning model. A result of whether the fourth sensing signal is a false trigger signal may be obtained by the machine learning model. If the fourth sensing signal is a false trigger signal, the target object may not need to perform any operation. If the fourth sensing signal is not a false trigger signal, a signal that an interval between the signal and the fourth sensing signal is within a range of another threshold time (e.g., 2 s, 3 s, 5 s, 10 s, etc.) may be designated as the sensing signal by the processing device 120. In some embodiments, the false trigger identification model may be a trained machine learning model. The training process of the false trigger identification model may be the same as or similar to the training process of the feature extraction model.

Figure 22:
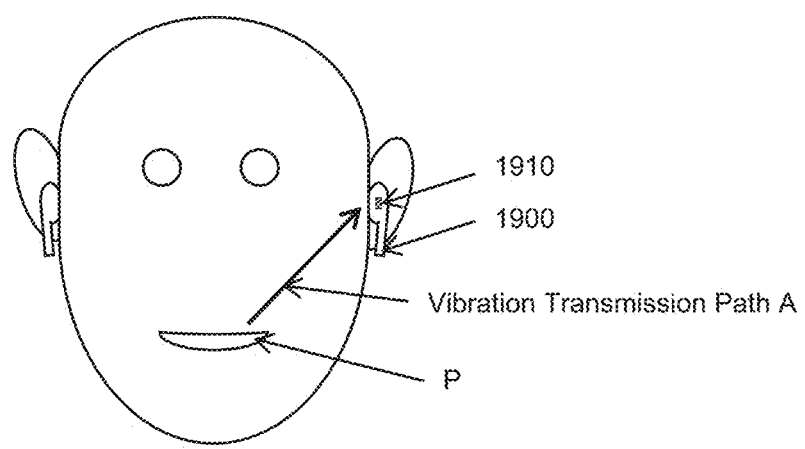
FIG. 22 is a schematic diagram illustrating that a system for controlling a target object is applied to a wearable device according to some embodiments of the present disclosure.

FIG. 22 is a schematic diagram illustrating that a system for controlling a target object is applied to a wearable device according to some embodiments of the present disclosure. One or more components or units of the system 100 for controlling a target object may be integrated on the headset 1900 or communicatively connected with the headset 1900.

Figure 23:
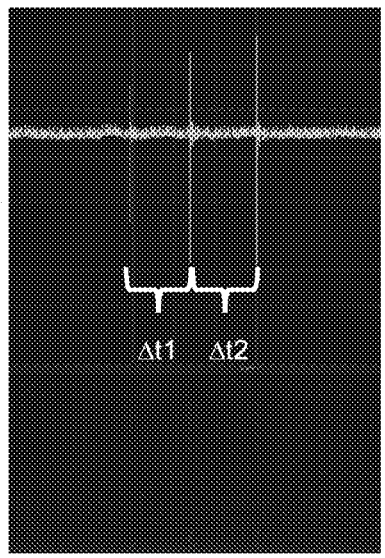
FIG. 23 is a schematic diagram illustrating a signal feature spectrum of a sensing signal corresponding to tooth tapping of a user according to some embodiments of the present disclosure.

As shown in FIG. 22, a vibration sensing device 1910 may be arranged at the right part of the headset 1900, and no vibration sensing device is arranged at the left part of the headset 1900. During a tooth tapping of the user, a vibration signal may be generated at a tapping point P. The vibration signal may be transmitted to the vibration sensing device 1910 via a vibration transmission path A. The vibration sensing device 1910 may generate a corresponding vibration sensing signal according to the collected vibration signal. The processing device 120 may identify a signal feature in the vibration sensing signal and determine whether the signal feature meets a predetermined feature condition. In some embodiments, the vibration sensing signal may be output as a signal feature spectrum. Based on the signal feature spectrum, the processing device 120 may identify the signal feature of the sensing signal. For example, the processing device 120 may read a count of vibration peaks, frequency components of the signal, etc. from the signal feature spectrum. FIG. 23 is a schematic diagram illustrating a signal feature spectrum of a sensing signal corresponding to tooth tapping of a user according to some embodiments of the present disclosure. As shown in FIG. 23, the sensing signal may include three vibration peaks. According to the time of signal collection/generation, a time interval between the two previous vibration peaks among the three vibration peaks may be $\Delta t1$, and a time interval between the two following vibration peaks among the three vibration peaks may be $\Delta t2$.

In some embodiments, the signal feature corresponding to a specific tooth tapping may be designated as a predetermined feature. An exemplary tooth tapping may include (1) twice consecutive tapping: $\Delta t$; (2) twice slow tapping: $t1 > \Delta t > t0$; (3) three times consecutive tapping: $\Delta t1$; (4) three times slow tapping: $t1 > \Delta t1 > t0$, $t1 > \Delta t2 > t0$; (5) twice consecutive tapping+once tapping: $\Delta t1 > \Delta t2 > t0$; (6) once slow tapping+twice consecutive tapping: $t1 > \Delta t1 > t0$, $\Delta t2$ $\Delta t$ denotes a time interval between two adjacent tapping (which may reflect a time interval between two vibration peaks). t0 denotes a first tapping interval threshold, and t1 denotes a second tapping interval threshold. In some embodiments, the first tapping interval threshold t0 may be 0.1 s~1 s. In some embodiments, the first tapping interval threshold t0 may be 0.15 s~0.9 s. In some embodiments, the first tapping interval threshold t0 may be 0.2 s~0.8 s. In some embodiments, the second tapping interval threshold t1 may be 0.8 s~5 s. In some embodiments, the second tapping interval threshold t1 may be 0.9 s~4 s. In some embodiments, the second tapping interval threshold t1 may be 1 s~2 s.

The signal feature of the sensing signal generated by the above tooth tapping may correspond to different operations of the target object, respectively. An exemplary operation may include power on/off, play/pause, get through/hang up calls, volume up/down, Bluetooth on/off, or the like. It should be noted that the above tooth tapping, the values of related parameters, and the operations of the corresponding target object may be merely by way of example, and may not limit the scope of the protection of the present disclosure.

In some embodiments, when the signal feature of the sensing signal generated by the tooth tapping of the user meets the specific predetermined feature condition, the processing device 120 may determine the operation of the target object corresponding to the specific predetermined feature, and control the target object (e.g., a terminal device, such as a headset 1900, a mobile phone, etc.) to perform the operation.

FIG. 24 is a schematic diagram illustrating that a system for controlling a target object is applied to a wearable device according to some embodiments of the present disclosure. Different from the embodiment described in FIG. 22, in this embodiment, left and right parts of a headset 1900 may include vibration sensing devices 1920 and 1910, respectively. The vibration sensing device 1910 may be the same as or similar to the vibration sensing device 1920. The vibration signal generated at a tooth tapping point P may be transmitted to the vibration sensing device 1920 at the left via a vibration transmission path B, and may be transmitted to the vibration sensing device 1910 at the right via a vibration transmission path A. The vibration sensing devices 1910 and 1920 may generate a sensing signal a and a sensing signal b, respectively. The processing device 120 may identify the signal feature of the sensing signal a and the sensing signal b (e.g., a count of vibration peaks of the sensing signal a/b, a time interval between two adjacent vibration peaks of the sensing signal a/b, a signal duration of the sensing signal a/b, and/or a phase difference of the sensing signal a and the sensing signal b) and determine whether the signal feature meets a predetermined feature condition.

In some embodiments, the signal feature corresponding to a specific tooth tapping may be designated as a predetermined feature condition. Through a left tooth, a right tooth, or a middle tooth (i.e., an incisor), an exemplary tooth tapping may include (1) twice consecutive tapping: $\Delta t$; (2) twice slow tapping: $t1 > \Delta t > t0$; (3) three times consecutive tapping: $\Delta t1$; (4) three times slow tapping: $t1 > \Delta t1 > t0$, $t1 > \Delta t2 > t0$; (5) twice consecutive tapping+once slow tapping: $\Delta t1 > \Delta t2 > t0$; (6) once slow tapping+twice consecutive tapping: $t1 > \Delta t1 > t0$, $\Delta t2$. In other examples, the tooth tapping may be completed by the cooperation of the left tooth, the right tooth, and the middle tooth. For example, (1) twice consecutive tapping on the left (that is, the left tooth)+once tapping on the right (that is, the right tooth): $\Delta t1 > \Delta t2 > t0$; (2) twice consecutive tapping on the left+once tapping on the middle (that is, the middle tooth): $\Delta t1 > \Delta t2 > t0$; (3) twice consecutive tapping on the right+once tapping on the left: $\Delta t1 > \Delta t2 > t0$; (4) twice consecutive tapping on the right+once tapping on the middle: $\Delta t1 > \Delta t2 > t0$; (5) twice consecutive tapping on the middle+once tapping on the right: $\Delta t1 > \Delta t2 > t0$; (6) twice consecutive tapping on the middle+once tapping on the left: $\Delta t1 > \Delta t2 > t0$; (7) once tapping on the left+twice consecutive tapping on the right: $t1 > \Delta t2 > t0$, $\Delta t2$; (8) once tapping on the left+twice consecutive tapping on the middle: $t1 > \Delta t2 > t0$, $\Delta t2$; (9) 1 tapping on the right+twice consecutive tapping on the left: $t1 > \Delta t2 > t0$, $\Delta t2$; (10) once tapping on the right+twice consecutive tapping on the middle: $t1 > \Delta t2 > t0$, $\Delta t2$; (11) once tapping on the right+twice consecutive tapping on the right: $t1 > \Delta t2 > t0$, $\Delta t2$; (12) once tapping on the middle+twice consecutive tapping on the left: $t1 > \Delta t2 > t0$, $\Delta t2$.

The signal features of the sensing signals generated by the above tooth tapping may correspond to different operations of the target object, respectively. An exemplary operation may include power on/off, play/pause, get through/hang up calls, dial/hang up emergency contacts, dial/hang up emergency centers, volume up/down, Bluetooth on/off, light brightness up/down, etc. It should be noted that the above tooth patting and the operations of the corresponding target object may be merely by way of example, and may not limit the scope of the protection of the present disclosure.

In some embodiments, when the signal feature of the sensing signal generated by the tooth tapping of the user meets the specific predetermined feature condition, the processing device 120 may determine the operation of the target object corresponding to the specific predetermined feature, and control the target object (e.g., a terminal device, such as a headset 1900, a mobile phone, etc.) to perform the operation.

Having thus described the basic concepts, it may be rather apparent to those skilled in the art after reading this detailed disclosure that the foregoing detailed disclosure is intended to be presented by way of example only and is not restrictive. Although not explicitly stated here, those skilled in the art may make various modifications, improvements and amendments to the present disclosure. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various parts of this specification are not necessarily all referring to the same embodiment. In addition, some features, structures, or features in the present disclosure of one or more embodiments may be appropriately combined.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, all aspects of the present disclosure may be performed entirely by hardware, may be performed entirely by software (including firmware, resident software, microcode, etc.), or may be performed by a combination of hardware and software. The above hardware or software may be referred to as "data block," "module," "engine," "unit," "component" or "system". In addition, aspects of the present disclosure may appear as a computer product located in one or more computer-readable media, the product including computer-readable program code.

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. However, this disclosure does not mean that the present disclosure object requires more features than the features mentioned in the claims. Rather, claimed subject matter may lie in less than all features of a single foregoing disclosed embodiment.

In some embodiments, the numbers expressing quantities of ingredients, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Finally, it should be understood that the embodiments described in the present disclosure merely illustrates the principles of the embodiments of the present disclosure. Other modifications may be within the scope of the present disclosure. Accordingly, by way of example, and not limitation, alternative configurations of embodiments of the present disclosure may be considered to be consistent with the teachings of the present disclosure. Accordingly, the embodiments of the present disclosure are not limited to the embodiments explicitly introduced and described by the present disclosure.

What is claimed is:

1. A system, comprising:
   at least one storage device configured to store computer instructions; and
   at least one processor in communication with the storage device, wherein when executing the computer instructions, the at least one processor is configured to direct the system to perform operations including:
      obtaining a sensing signal of at least one sensing device, the at least one sensing device including a vibration sensing device and an audio input device, the vibration sensing device being arranged on a wearable device, the wearable device being attached to a body part of a user, and the vibration sensing device receiving the sensing signal that is a vibration signal generated by a body activity of the user through the wearable device;
      determine whether the audio input device simultaneously receives user audio information when the vibration sensing device receives the sensing signal; and
      in response to a determination that the audio input device receives user audio information, designating the sensing signal as a false trigger signal;
      in response to a determination that the audio input device does not receive user audio information, identifying a signal feature of the sensing signal; and
      determining, based on the signal feature, an operation of a target object associated with the at least one sensing device.

2. The system of claim 1, wherein the signal feature include at least one of a count of vibration peaks, a signal strength, a time interval between two adjacent vibration peaks, frequency components, or a signal duration.

3. The system of claim 1, wherein the vibration sensing device is connected to a vibration receiving area through a solid medium, and receives a vibration signal input to the vibration receiving area.

4. The system of claim 3, wherein the vibration signal is input to the vibration receiving area by knocking, patting, or scraping in the vibration receiving area.

5. The system of claim 3, wherein the vibration sensing device is fixedly connected to the solid medium through at least one of bonding, inlaying, welding, riveting, or screw connection.

6. The system of claim 1, wherein the obtaining a sensing signal of at least one sensing device includes:
   obtaining a first sensing signal of the at least one sensing device;
   determining whether the first sensing signal is greater than a signal threshold; and
   in response to a determination that the first sensing signal is greater than the signal threshold, designating a signal that an interval between the signal and the first sensing signal is within a range of a threshold time as the sensing signal.

7. The system of claim 1, wherein the vibration sensing device is attached to a body part of a user, and the vibration sensing device receives the vibration signal generated by the body activity of the user.

8. The system of claim 1, wherein the body activity includes coughing, sneezing, snoring, yawning, or falling.

9. The system of claim 1, wherein the determining, based on the signal feature, an operation of a target object associated with the at least one sensing device includes:
   determining, based on the signal feature, a physiological status of the user; and
   determining, based on the physiological status of the user, the operation of the target object corresponding to the physiological status.

10. The system of claim 9, the determining, based on the signal feature, a physiological status of the user includes:
    determining whether the signal feature meets a predetermined feature, the signal feature being a feature of the vibration signal generated by the body activity of the user; and
    in response to the determination that the signal feature meets the predetermined feature, determining the physiological status corresponding to the predetermined feature.

11. The system of claim 1, wherein the operation of the target object includes a mobile terminal recording a health status or issuing an early warning.

12. The system of claim 1, wherein the body activity includes a tooth tapping.

13. The system of claim 12, wherein the operation of the target object includes switching the terminal device from a first state to a second state.

14. The system of any of claim 12, wherein the obtaining a sensing signal of at least one sensing device includes:
    obtaining a second sensing signal of the at least one sensing device;
    determining whether a frequency of the second sensing signal is lower than a frequency threshold; and
    in response to a determination that the frequency of the second sensing signal is lower than the frequency threshold, designating the second sensing signal as a false trigger signal.

15. The system of claim 12, wherein the obtaining a sensing signal of at least one sensing device includes:
  obtaining a fourth sensing signal of the at least one sensing device;
  determining, based on a false trigger identification model, whether the fourth sensing signal is the false trigger signal; and
  in response to a determination that the fourth sensing signal is not the false trigger signal, designating a signal that an interval between the signal and the fourth sensing signal is within a range of another threshold time as the sensing signal.

16. A method, comprising:
  obtaining a sensing signal of at least one sensing device, the at least one sensing device including a vibration sensing device and an audio input device, the vibration sensing device being arranged on a wearable device, the wearable device being attached to a body part of a user, and the vibration sensing device receiving the sensing signal that is a vibration signal generated by a body activity of the user through the wearable device;
  determine whether the audio input device simultaneously receives user audio information when the vibration sensing device receives the sensing signal; and
  in response to a determination that the audio input device receives user audio information, designating the sensing signal as a false trigger signal;
  in response to a determination that the audio input device does not receive user audio information,
    identifying a signal feature of the sensing signal, wherein the signal feature includes at least one of a count of vibration peaks, a signal strength, a time interval between two adjacent vibration peaks, frequency components, or a signal duration; and
    determining, based on the signal feature, an operation of a target object associated with the at least one sensing device.

17. A non-transitory computer-readable medium, comprising
  at least one set of computer instructions,
  wherein when executed by at least one processor, the at least one set of computer instructions direct the at least one processor to perform operations including:
  obtaining a sensing signal of at least one sensing device, the at least one sensing device including a vibration sensing device and an audio input device, the vibration sensing device being arranged on a wearable device, the wearable device being attached to a body part of a user, and the vibration sensing device receiving the sensing signal that is a vibration signal generated by a body activity of the user through the wearable device;
  determine whether the audio input device simultaneously receives user audio information when the vibration sensing device receives the sensing signal; and
  in response to a determination that the audio input device receives user audio information, designating the sensing signal as a false trigger signal;
  in response to a determination that the audio input device does not receive user audio information,
    identifying a signal feature of the sensing signal, wherein the signal feature includes at least one of a count of vibration peaks, a signal strength, a time interval between two adjacent vibration peaks, frequency components, or a signal duration; and
    determining, based on the signal feature, an operation of a target object associated with the at least one sensing device.

* * * * *